US012256889B2

United States Patent
Kitamura et al.

(10) Patent No.: US 12,256,889 B2
(45) Date of Patent: Mar. 25, 2025

(54) ENDOSCOPIC IMAGE PROCESSING APPARATUS, ENDOSCOPIC IMAGE PROCESSING METHOD, AND RECORDING MEDIUM

(71) Applicant: OLYMPUS CORPORATION, Tokyo (JP)

(72) Inventors: Makoto Kitamura, Hachioji (JP); Yamato Kanda, Hino (JP); Katsuyoshi Taniguchi, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 1210 days.

(21) Appl. No.: 16/936,601

(22) Filed: Jul. 23, 2020

(65) Prior Publication Data
US 2021/0000327 A1    Jan. 7, 2021

Related U.S. Application Data

(63) Continuation of application No. PCT/JP2018/002462, filed on Jan. 26, 2018.

(51) Int. Cl.
*A61B 1/00* (2006.01)
*G06T 7/00* (2017.01)
*G06T 7/70* (2017.01)

(52) U.S. Cl.
CPC ...... *A61B 1/000094* (2022.02); *A61B 1/0005* (2013.01); *G06T 7/0012* (2013.01);
(Continued)

(58) Field of Classification Search
CPC .............. A61B 1/000094; A61B 1/0005
See application file for complete search history.

(56) References Cited

U.S. PATENT DOCUMENTS

| 6,293,911 B1 * | 9/2001 | Imaizumi ......... A61B 1/000094 600/178 |
| 2004/0090472 A1 * | 5/2004 | Risch ................ G06F 16/9038 707/E17.093 |

(Continued)

FOREIGN PATENT DOCUMENTS

| JP | 2017-213097 A | 12/2017 |
| WO | WO 2017/073338 A1 | 5/2017 |

OTHER PUBLICATIONS

International Search Report dated Apr. 17, 2018 issued in PCT/JP2018/002462.

*Primary Examiner* — Aaron B Fairchild
(74) *Attorney, Agent, or Firm* — Scully, Scott, Murphy & Presser, P.C.

(57) ABSTRACT

An endoscopic image processing apparatus is configured to generate a display image including one main screen and one or more sub-screens smaller than the main screen for displaying an endoscopic image obtained by picking up an image of an object in a subject with an endoscope. The endoscopic image processing apparatus includes a processor. The processor receives the endoscopic image and detects one or more lesion candidate regions included in the endoscopic image, highlights a position of the lesion candidate region, and sets, based on any one of a state of the lesion candidate region, a work state of a user who performs work using the endoscope, or a display state of the display image, a highlighting method in highlighting a position of the lesion candidate region included in at least one of the main screen or the sub-screen.

14 Claims, 14 Drawing Sheets

(52) U.S. Cl.
CPC ...... *G06T 7/70* (2017.01); *G06T 2207/10068* (2013.01); *G06T 2207/30096* (2013.01)

(56) References Cited

U.S. PATENT DOCUMENTS

2012/0327205 A1* 12/2012 Takahashi ........ A61B 1/000094
  348/65
2019/0197738 A1* 6/2019 Kishita .................... G06T 7/90

* cited by examiner

ENDOSCOPIC IMAGE PROCESSING APPARATUS, ENDOSCOPIC IMAGE PROCESSING METHOD, AND RECORDING MEDIUM

CROSS REFERENCE TO RELATED APPLICATION

This application is a continuation application of PCT/JP2018/002462 filed on Jan. 26, 2018, the entire contents of which are incorporated herein by this reference.

BACKGROUND OF THE INVENTION

1. Field of the Invention

The present invention relates to an endoscopic image processing apparatus, an endoscopic image processing method, and a recording medium.

2. Description of the Related Art

In endoscopic observation in a medical field, a technique has been known for detecting a lesion candidate region from an endoscopic image obtained by picking up an image of a desired part in a subject, adding visual information for informing presence of the detected lesion candidate region to the endoscopic image, and displaying the visual information.

More specifically, for example, International Publication No. 2017/073338 discloses a technique for detecting a lesion candidate region from an observation image obtained by picking up an image of an inside of a subject with an endoscope, adding a marker image surrounding the detected lesion candidate region to the observation image, and thereby displaying a display image in which a position of the lesion candidate region in the observation image is highlighted. International Publication No. 2017/073338 also discloses a configuration for causing a main screen and a sub-screen to simultaneously display a movie equivalent to an observation image obtained by picking up an image of an inside of a subject with an endoscope.

SUMMARY OF THE INVENTION

An endoscopic image processing apparatus according to an aspect of the present invention is an endoscopic image processing apparatus configured to generate a display image including one main screen and one or more sub-screens smaller than the main screen for displaying an endoscopic image obtained by picking up an image of an object in a subject with an endoscope, the endoscopic image processing apparatus including a processor. The processor is configured to receive the endoscopic image and detect one or more lesion candidate regions included in the endoscopic image, highlight a position of the lesion candidate region, and set, based on any one of a state of the lesion candidate region, a work state of a user who performs work using the endoscope, or a display state of the display image, a highlighting method in highlighting a position of the lesion candidate region included in at least one of the main screen or the sub-screen.

An endoscopic image processing method according to an aspect of the present invention is an endoscopic image processing method used in an endoscopic image processing apparatus configured to generate a display image including one main screen and one or more sub-screens smaller than the main screen for displaying an endoscopic image obtained by picking up an image of an object in a subject with an endoscope, the endoscopic image processing method including: detecting one or more lesion candidate regions included in the endoscopic image; highlighting a position of the lesion candidate region; and setting, based on any one of a state of the lesion candidate region, a work state of a user who performs work using the endoscope, or a display state of the display image, a highlighting method in highlighting, by processing of the highlighting processing section, a position of the lesion candidate region included in at least one of the main screen or the sub-screen.

A computer-readable non-transitory recording medium recording an image processing program according to an aspect of the present invention, the computer-readable non-transitory recording medium causing a computer to execute: processing for generating a display image including one main screen and one or more sub-screens smaller than the main screen for displaying an endoscopic image obtained by picking up an image of an object in a subject with an endoscope; processing for detecting one or more lesion candidate regions included in the endoscopic image; processing for highlighting a position of the lesion candidate region; and processing for setting, based on any one of a state of the lesion candidate region, a work state of a user who performs work using the endoscope, or a display state of the display image, a highlighting method in highlighting a position of the lesion candidate region included in at least one of the main screen or the sub-screen.

DETAILED DESCRIPTION OF THE PREFERRED EMBODIMENTS

Embodiments of the present invention are explained below with reference to the drawings.

First Embodiment

FIG. 1 to FIG. 6 relate to a first embodiment of the present invention.

Figure 1:
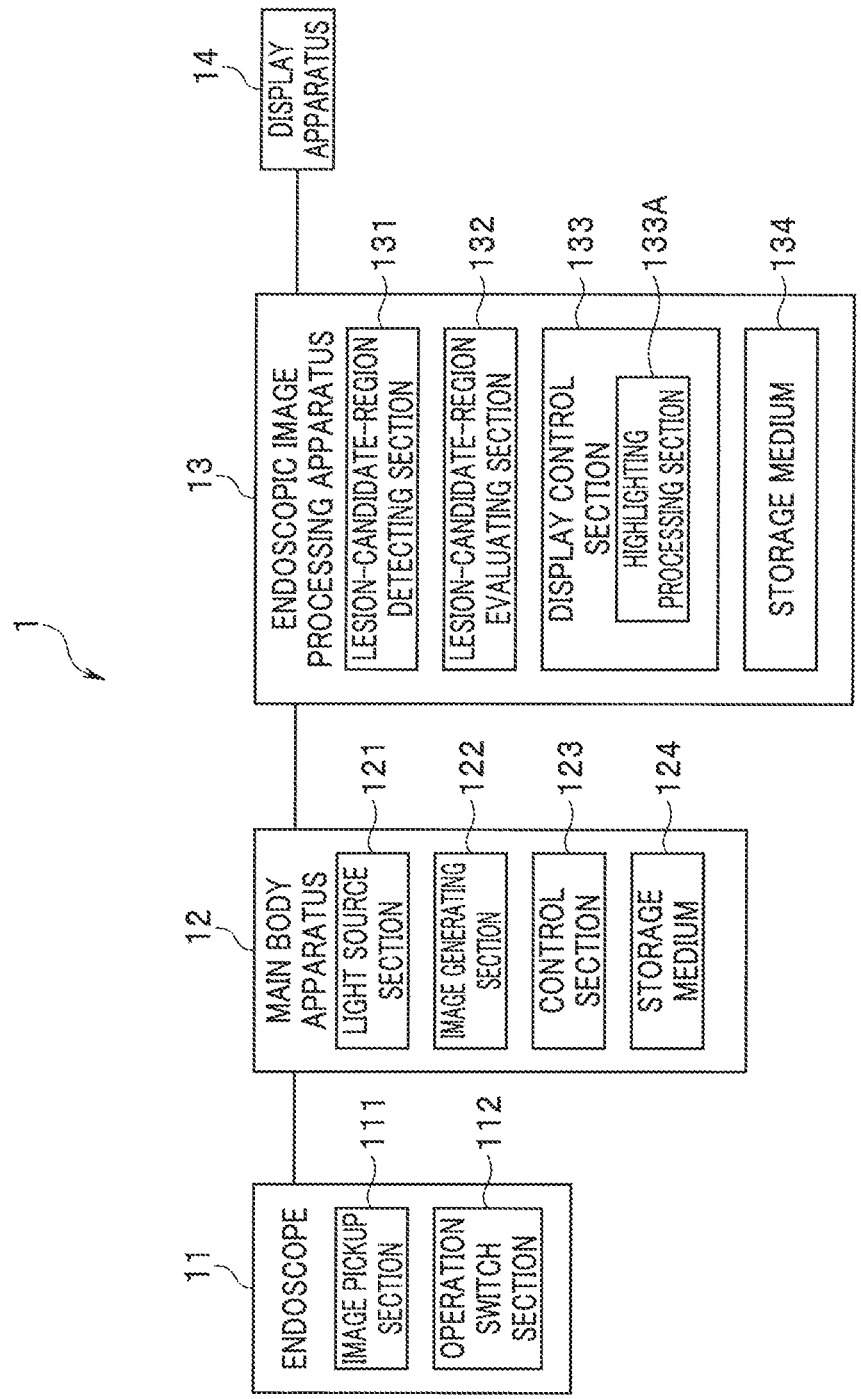
FIG. 1 is a diagram showing a configuration of a main part of an endoscope system including an endoscopic image processing apparatus according to a first embodiment.

An endoscope system 1 includes, as shown in FIG. 1, an endoscope 11, a main body apparatus 12, an endoscopic imam processing apparatus 13, and a display apparatus 14. FIG. 1 is a diagram showing a configuration of a main part of an endoscope system including an endoscopic image processing apparatus according to the first embodiment.

The endoscope 11 includes, for example, an elongated insertion section (not illustrated) insertable into a subject and an operation section (not illustrated) provided at a proximal end portion of the insertion section. For example, the endoscope 11 is detachably connected to the main body apparatus 12 via a universal cable (not illustrated) extending from the operation section. A light guide member (not illustrated) such as an optical fiber for guiding illumination light supplied from the main body apparatus 12 and emitting the illumination light from a distal end portion of the insertion section is provided on an inside of the endoscope 11. The endoscope 11 includes an image pickup section 111 provided at the distal end portion of the insertion section and an operation switch section 112 provided in the operation section.

The image pickup section 111 includes, for example, a CCD image sensor or a CMOS image sensor. The image pickup section 111 is configured to pick up an image of return light from an object illuminated by the illumination light emitted through the distal end portion of the insertion section, generate an image pickup signal corresponding to the return light, the image of which is picked up, and output the image pickup signal to the main body apparatus 12.

The operation switch section 112 includes one or more switches capable of giving instructions corresponding to operation by a user to the main body apparatus 12. More specifically, for example, switches for giving instructions relating to setting of observation magnification of the endoscope 11 (the image pickup section 111) are provided in the operation switch section 112. In other words, one or more switches capable of giving instructions for setting operation states of one or more functions included in the endoscope 11 are provided in the operation switch section 112.

The main body apparatus 12 is detachably connected to each of the endoscope 11 and the endoscopic image processing apparatus 13. The main body apparatus 12 includes, for example, as shown in FIG. 1, a light source section 121, an image generating section 122, a control section 123, and a storage medium 124.

The light source section 121 includes one or more light emitting elements such as LEDs. More specifically, the light source section 121 includes, for example, a blue LED that generates blue light (hereinafter referred to as B light as well), a green LED that generates green light (hereinafter referred to as G light as well), and a red LED that generates red light (hereinafter referred to as R light as well). The light source section 121 is configured to be able to generate illumination light corresponding to control by the control section 123 and supply the illumination light to the endoscope 11.

The image generating section 122 is configured to be able to generate an endoscopic image based on an image pickup signal outputted from the endoscope 11 and sequentially output the generated endoscopic image to the endoscopic image processing apparatus 13 frame by frame.

The control section 123 is configured to perform, based on an instruction or the like given by the operation switch section 112, control relating to operation of sections of the endoscope 11 and the main body apparatus 12.

In the present embodiment, the image generating section 122 and the control section 123 of the main body apparatus 12 may be configured as individual electronic circuits or may be configured as circuit blocks in an integrated circuit such as an FPGA (field programmable gate array). In the present embodiment, for example, the main body apparatus 12 may include one or more CPUs. By modifying the configuration according to the present embodiment as appropriate, for example, the main body apparatus 12 may read, from the storage medium 124 such as a memory, a program for executing functions of the image generating section 122 and the control section 123, and may perform operation corresponding to the read program.

The endoscopic image processing apparatus 13 is a processor detachably connected to each of the main body apparatus 12 and the display apparatus 14. The endoscopic image processing apparatus 13 includes a lesion-candidate-region detecting section 131, a lesion-candidate-region evaluating section 132, a display control section 133, and a storage medium 134. The lesion-candidate-region detecting section 131, the lesion-candidate-region evaluating section 132, and the display control section 133 are circuits that perform control of the sections in the endoscopic image processing apparatus 13. Note that functions of these circuits may be realized by software. In this case, the endoscopic image processing apparatus 13 includes a central processing unit (CPU), ROM, and RAM and the like, and executes programs of the functions, whereby functions of the lesion-candidate-region detecting section 131, the lesion-candidate-region evaluating section 132, and the display control section 133 are realized. Note that when the functions of the sections are realized by software, a part of the sections may be realized by integral hardware. As the processor, besides the CPU (central processing unit), various processors such as a DSP (digital signal processor) can be used. The processor may be a hardware circuit by an ASIC (application specific integrated circuit) or an FPGA (field programmable gate array).

The lesion-candidate-region detecting section 131 is configured to perform processing for detecting a lesion candidate region L included in endoscopic images sequentially outputted from the main body apparatus 12 and perform processing for acquiring lesion candidate information IL, which is information indicating the detected lesion candidate region L. In other words, endoscopic images obtained by picking up an image of an object in a subject with an endoscope are sequentially inputted to the lesion-candidate-region detecting section 131. The lesion-candidate-region detecting section 131 is configured to perform processing for detecting one or a plurality of lesion candidate regions L included in the endoscopic images.

Note that, in the present embodiment, the lesion candidate region L is detected as, for example, a region including a polyp. In the present embodiment, the lesion candidate information IL is acquired as, for example, information including position information indicating a position (a pixel position) of the lesion candidate region L included in an endoscopic image outputted from the main body apparatus 12 and size information indicating a size (the number of pixels) of the lesion candidate region L included in the endoscopic image.

In the present embodiment, for example, the lesion-candidate-region detecting section 131 may be configured to detect the lesion candidate region L based on a predetermined feature value obtained from an endoscopic image obtained by picking up an image of an object in a subject with an endoscope or may be configured to detect the lesion candidate region L using a discriminator that has acquired, in advance, with a learning method such as deep learning, a function capable of discriminating an abnormal finding included in the endoscopic image.

The lesion-candidate-region evaluating section 132 is configured to perform processing for evaluating a state of the lesion candidate region L detected by the lesion-candidate-region detecting section 131. Note that a specific example of the processing performed in the lesion-candidate-region evaluating section 132 is explained below.

The display control section 133 is configured to perform processing for generating, based on the endoscopic images sequentially outputted from the main body apparatus 12 and display setting information (explained below) read from the storage medium 134, a display image including the endoscopic images in each of one main screen (explained below) and one or more sub-screens (explained below) and processing for causing the display apparatus 14 to display the generated display image. The display control section 133 includes a highlighting processing section 133A that performs highlighting processing for highlighting a position of the lesion candidate region L detected from the endoscopic image by the processing of the lesion-candidate-region detecting section 131. The display control section 133 is configured to perform processing relating to setting of a marker image M (explained below) added by the highlighting processing of the highlighting processing section 133A.

The highlighting processing section 133A is configured to generate, based on the legion candidate information IL acquired by the lesion-candidate-region detecting section 131, the marker image M for highlighting the position of the lesion candidate region L detected from the endoscopic image by the processing of the lesion-candidate-region detecting section 131 and perform, as the highlighting processing, processing for adding the generated marker image M to the endoscopic image. Note that, as long as the highlighting processing section 133A generates the marker image M for highlighting the position of the lesion candidate region L, the highlighting processing section 133A may perform the highlighting processing using only the position information included in the lesion candidate information IL or may perform the highlighting processing using both of the position information and the size information included in the lesion candidate information IL.

In the storage medium 134, display setting information including one or more setting values relating to the display image generated by the display control section 133 is stored.

More specifically, the display setting information stored in the storage medium 134 includes, for example, information indicating a setting value of brightness of an entire display image including a main screen and sub-screens generated by the display control section 133, information indicating a setting value of a screen size of the main screen, and information indicating a setting value of a screen size of the sub-screens.

Note that the setting values stored in the storage medium 134 may be preset fixed values or may be variable values changeable by the user.

In the present embodiment, the sections of the endoscopic image processing apparatus 13 may be configured as individual electronic circuits or may be configured as circuit blocks in an integrated circuit such as an FPGA (field programmable gate array). In the present embodiment, for example, the endoscopic image processing apparatus 13 may include one or more CPUs. By modifying the configuration according to the present embodiment as appropriate, for example, the endoscopic image processing apparatus 13 may read, from the storage medium 134 such as a memory, a program for executing functions of the lesion-candidate-region detecting section 131, the lesion-candidate-region evaluating section 132, and the display control section 133, and may perform operation corresponding to the read program. By modifying the configuration according to the present embodiment as appropriate, for example, the functions of the sections of the endoscopic image processing apparatus 13 may be incorporated as functions of the main body apparatus 12.

The display apparatus 14 includes a monitor or the like and is configured to be able to display a display image outputted through the endoscopic image processing apparatus 13.

Next, action of the present embodiment is explained. Note that, in the following explanation, unless particularly referred to, a case is explained, as an example, in which B light, G light, and R light are sequentially or simultaneously emitted from the light source section 121 as illumination light corresponding to the control by the control section 123, that is, an endoscopic image including color components of blue, green, and red is generated by the image generating section 122.

After connecting the sections of the endoscope system 1 and turning on a power supply, the user such as a surgeon inserts the insertion section of the endoscope 11 into an inside of a subject and arranges the distal end portion of the insertion section in a position where an image of a desired object on the inside of the subject can be picked up.

According to such operation by the user, illumination light is supplied from the light source section 121 to the endoscope 11. An image of return light from the object illuminated by the illumination light is picked up in the image pickup section 111. An endoscopic image corresponding to an image pickup signal outputted from the image pickup section 111 is generated in the image generating section 122 and is outputted to the endoscopic image processing apparatus 13.

Figure 2:
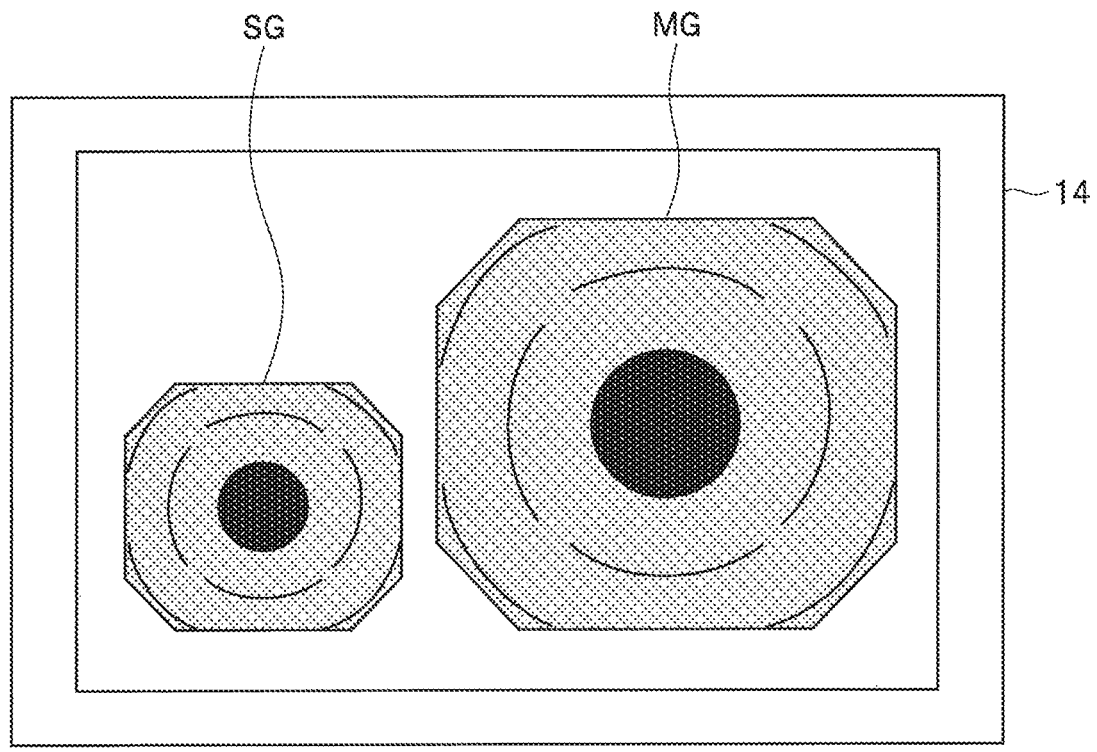
FIG. 2 is a diagram showing an example of a display image including a main screen and a sub-screen.

The display control section 133 generates a main screen MG by processing the endoscopic image based on the endoscopic image outputted from the main body apparatus 12 and the display setting information read from the storage medium 134 to match a setting value SL of a screen size of the main screen included in the display setting information and generates a sub-screen SG by processing the endoscopic image to match a setting value SS (<SL) of a screen size of a sub-screen included in the display setting information. Thereafter, the display control section 133 performs processing for generating a display image including the main screen MG and the sub-screen SG for simultaneously displaying the endoscopic image obtained by picking up the image of the object in the subject with the endoscope 11 and performs processing for causing the display apparatus 14 to display the generated display image. With such processing, for example, when the lesion candidate region L is not included in the endoscopic image outputted from the main body apparatus 12, a display image shown in FIG. 2 is displayed on the display apparatus 14. Note that, in the present embodiment, a display image different from the display image illustrated in FIG. 2 may be generated as long as one main screen MG and one or more sub-screens SG are included in the display image. FIG. 2 is a diagram showing an example of a display image including a main screen and a sub-screen.

Figure 3:
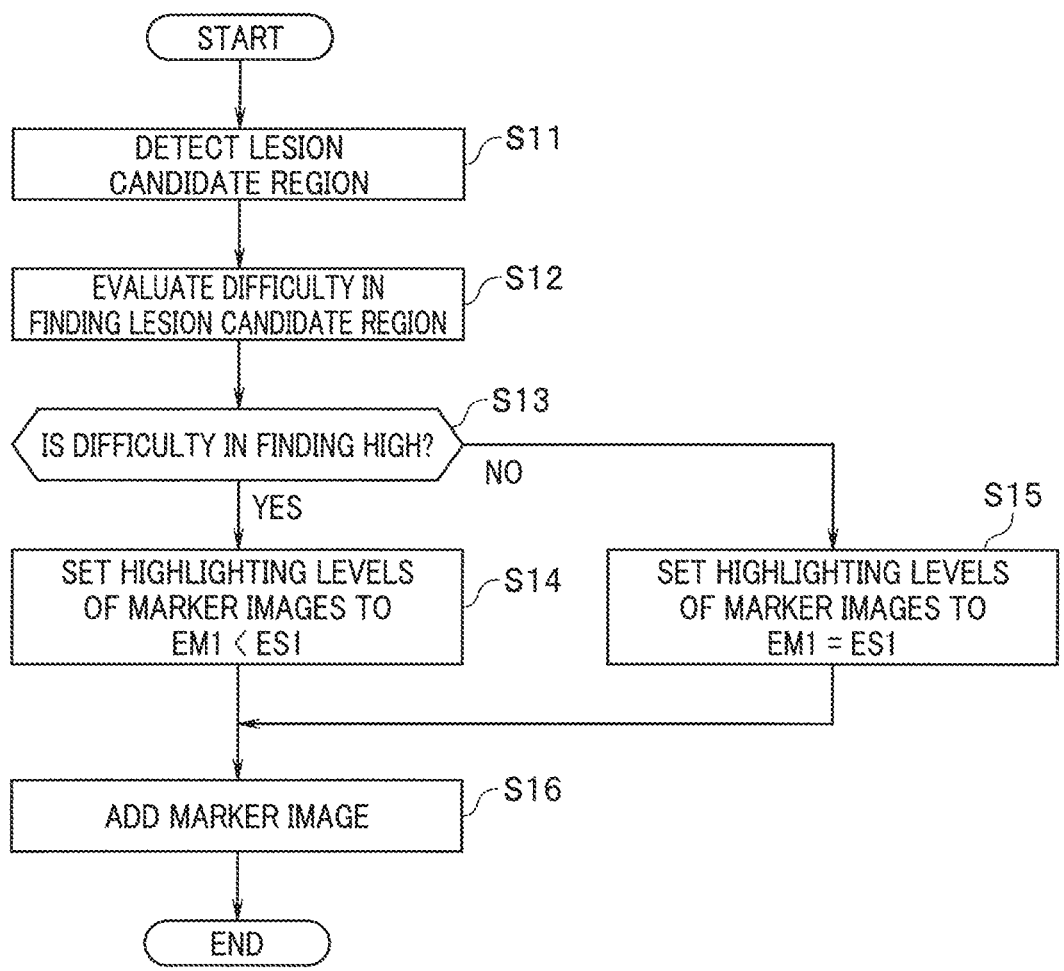
FIG. 3 is a flowchart for explaining a specific example of processing performed in the endoscopic image processing apparatus according to the first embodiment.

Specific examples of processing performed in the sections of the endoscopic image processing apparatus 13 in the present embodiment are explained with reference to FIG. 3 and the like. Note that, in the present embodiment, a case is explained, as an example, in which one lesion candidate region L is included in the endoscopic image outputted from the main body apparatus 12. FIG. 3 is a flowchart for explaining a specific example of processing performed in the endoscopic image processing apparatus according to the first embodiment.

The lesion-candidate-region detecting section 131 performs processing for detecting the lesion candidate region L included in the endoscopic image outputted from the main body apparatus 12 and performs processing for acquiring the lesion candidate information IL, which is information indicating the detected lesion candidate region L (step S11 in FIG. 3).

More specifically, for example, the lesion-candidate-region detecting section 131 performs the processing in step S11 in FIG. 3 to thereby detect a lesion candidate region L11 included in the endoscopic image outputted from the main body apparatus 12 and acquires lesion candidate information IL11, which is information indicating the detected lesion candidate region L11.

The lesion-candidate-region evaluating section 132 performs processing for evaluating difficulty in finding the lesion candidate region L based on at least one of the endoscopic image in which the lesion candidate region L is detected by the processing in step S11 in FIG. 3 or the legion candidate information IL corresponding to the lesion candidate region L (step S12 in FIG. 3).

A specific example of the processing performed in step S12 in FIG. 3 is explained.

For example, the lesion-candidate-region evaluating section 132 respectively detects a texture and a shape of the lesion candidate region L11 based on the endoscopic image in which the lesion candidate region L11 is detected by the processing in step S11 in FIG. 3 and position information included in lesion candidate information IL1 corresponding to the lesion candidate region L11. When determining based on a detection result of the texture and the shape of the lesion candidate region L11 that, for example, a flat polyp is included in the lesion candidate region L11, the lesion-candidate-region evaluating section 132 acquires an evaluation result indicating that the difficulty in finding the lesion candidate region L11 is high.

For example, the lesion-candidate-region evaluating section 132 detects strength of an edge in a boundary portion of the legion candidate region L11 based on the endoscopic image in which the lesion candidate region L11 is detected by the processing in step S11 in FIG. 3 and the position information included in the lesion candidate information IL11 corresponding to the lesion candidate region L11. For example, when detecting that the strength of the edge in the boundary portion of the lesion candidate region L11 is low, the lesion-candidate-region evaluating section 132 determines that a light-colored polyp is included in the lesion candidate region L11 and acquires an evaluation result indicating that the difficulty in finding the lesion candidate region L11 is high.

When determining that both of a flat polyp and a light-colored polyp are not included in the lesion candidate region L11, the lesion-candidate-region evaluating section 132 acquires an evaluation result indicating that the difficulty in finding the lesion candidate region L11 is low.

For example, the lesion-candidate-region evaluating section 132 acquires, based on size information included in the lesion candidate information IL11 acquired by the processing in step S11 in FIG. 3, a size in the endoscopic image of the lesion candidate region L11 detected by the processing in step S11 in FIG. 3. For example, when detecting that the size of the lesion candidate region L11 is equal to or smaller than a predetermined size, the lesion-candidate-region evaluating section 132 acquires an evaluation result indicating that the difficulty in finding the lesion candidate region L11 is high. For example, when detecting that the size of the lesion candidate region L11 is larger than the predetermined size, the lesion-candidate-region evaluating section 132 acquires an evaluation result indicating that the difficulty in finding the lesion candidate region L11 is low.

For example, the lesion-candidate-region evaluating section 132 acquires, based on the position information included in the lesion candidate information IL11 acquired by the processing in step S11 in FIG. 3, a position in the endoscopic image of the lesion candidate region L11 detected by the processing in step S11 in FIG. 3. For example, when detecting that at least a part of the lesion candidate region L11 is present on the outer side of the endoscopic image, the lesion-candidate-region evaluating section 132 acquires an evaluation result indicating that the difficulty in finding the lesion candidate region L11 is high. For example, when detecting that the entire lesion candidate region L11 is present in the endoscopic image, the lesion-candidate-region evaluating section 132 acquires an evaluation result indicating that the difficulty in finding the lesion candidate region L11 is low.

Note that, in the present embodiment, the difficulty in finding the lesion candidate region L may be evaluated by combining, as appropriate, a plurality of approaches among the specific examples explained above. More specifically, when a flat polyp or a light-colored polyp is included in the lesion candidate region L11 detected from the endoscopic image, when the size of the lesion candidate region L11 is equal to or smaller than the predetermined size, or when at least a part of the lesion candidate region L11 is present on the outer side of the endoscopic image, the lesion-candidate-region evaluating section 132 may acquire an evaluation result indicating that the difficulty in finding the lesion candidate region L11 is high. For example, when both of a flat polyp or a light-colored polyp are not included in the lesion candidate region L11 detected from the endoscopic image, the size of the lesion candidate region L11 is larger than the predetermined size, and when the entire lesion candidate region L11 is present in the endoscopic image, the lesion-candidate-region evaluating section 132 may acquire an evaluation result indicating that the difficulty in finding the lesion candidate region L11 is low.

In other words, according to the specific example explained above, the lesion-candidate-region evaluating section 132 performs the processing for evaluating the difficulty in finding the lesion candidate region L11 based on at least one of a type of a lesion included in the lesion candidate region L11 detected from the endoscopic image, the size in the endoscopic image of the lesion candidate region L11, or the position in the endoscopic image of the lesion candidate region L11.

The display control section 133 performs processing for respectively setting a marker image MM1 for highlighting, on the main screen MG, the position of the lesion candidate region L11 detected by the processing in step S11 in FIG. 3 and a marker image MS1 for highlighting, on the sub-screen SG, the position of the lesion candidate region L11. The display control section 133 performs processing for respectively setting, according to the evaluation result of the difficulty in finding the lesion candidate region L acquired by the processing in step S12 in FIG. 3, a highlighting level EM1 of the marker image MM1 added to the main screen MG and a highlighting level ES1 of the marker image MS1 added to the sub-screen SG (steps S13 to S15 in FIG. 3).

When detecting that the evaluation result indicating that the difficulty in finding the lesion candidate region L is high is obtained (S13: YES), for example, the display control section 133 performs setting the highlighting level EM1 of the marker image MM1 to a predetermined highlighting level and performs setting the highlighting level ES1 of the marker image MS1 higher than the predetermined highlighting level (step S14 in FIG. 3).

When detecting that the evaluation result indicating that the difficulty in finding the lesion candidate region L is low is obtained (S13: NO), for example, the display control section 133 performs setting the highlighting level EM1 of the marker image. MM1 to the predetermined highlighting level and performs setting the highlighting level ES1 of the marker image MS1 equal to the predetermined highlighting level (step S15 in FIG. 3).

In other words, the display control section 133 performs processing for setting, based on the evaluation result of the difficulty in finding the lesion candidate region L11 obtained by the processing of the lesion-candidate-region evaluating section 132 in step S13 to step S15 in FIG. 3, a highlighting method in highlighting positions of the lesion candidate region L11 included in the main screen MG and the sub-screen SG with processing of a highlighting processing section 133A.

The highlighting processing section 133A performs processing for generating, based on the lesion candidate information IL acquired by the processing in step S11 in FIG. 3, the marker images MM1 and MS1 set through the processing in step S14 or step S15 in FIG. 3, adding the generated marker image MM1 to the main screen MG, and adding the generated marker image MS1 to the sub-screen SG (step S16 in FIG. 3).

More specifically, for example, the highlighting processing section 133A performs processing for generating, based on the lesion candidate information IL11, the marker image MS1 having the highlighting level EM1 set by the processing in step S14 in FIG. 3 and adding the generated marker image MM1 to a periphery of the lesion candidate region L11 on the main screen MG. For example, the highlighting processing section 133A performs processing for generating, based on the lesion candidate information IL11, the marker image MS1 having the highlighting level ES1 set to be higher than the highlighting level EM1 by the processing in step S14 in FIG. 3 and adding the generated marker image MS1 to the periphery of the lesion candidate region L11 on a sub-screen MS1.

Figure 4:
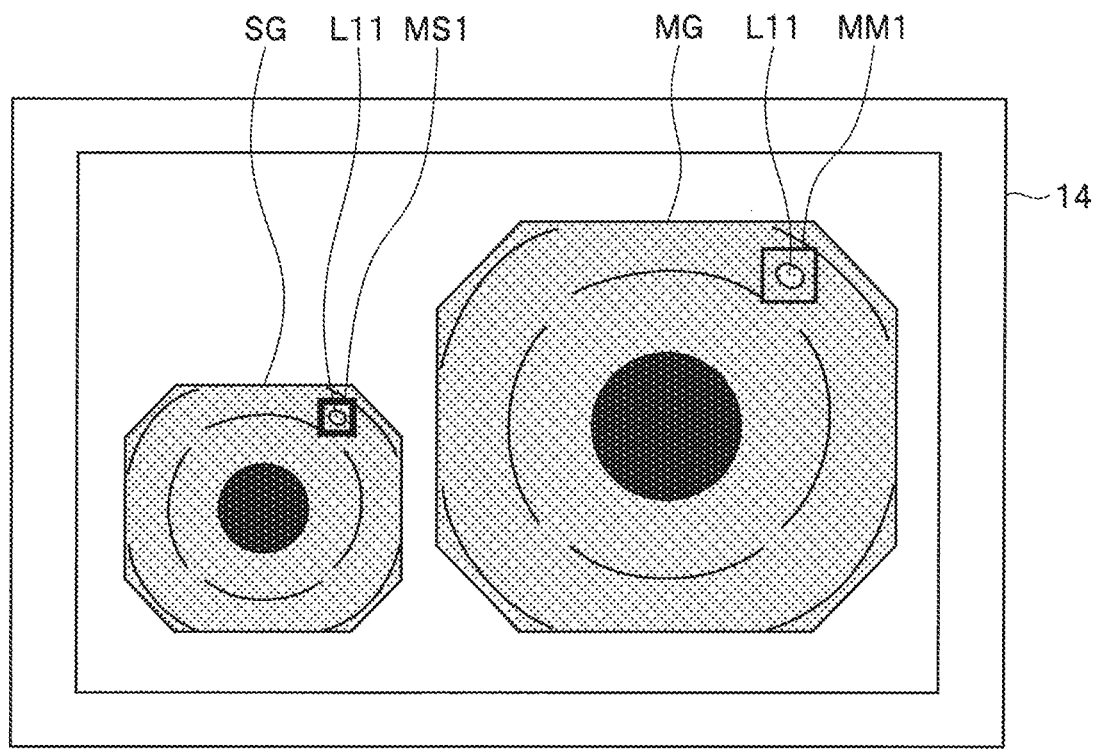
FIG. 4 is a diagram showing an example of a display image displayed according to the processing of the endoscopic image processing apparatus according to the first embodiment.
Figure 5:
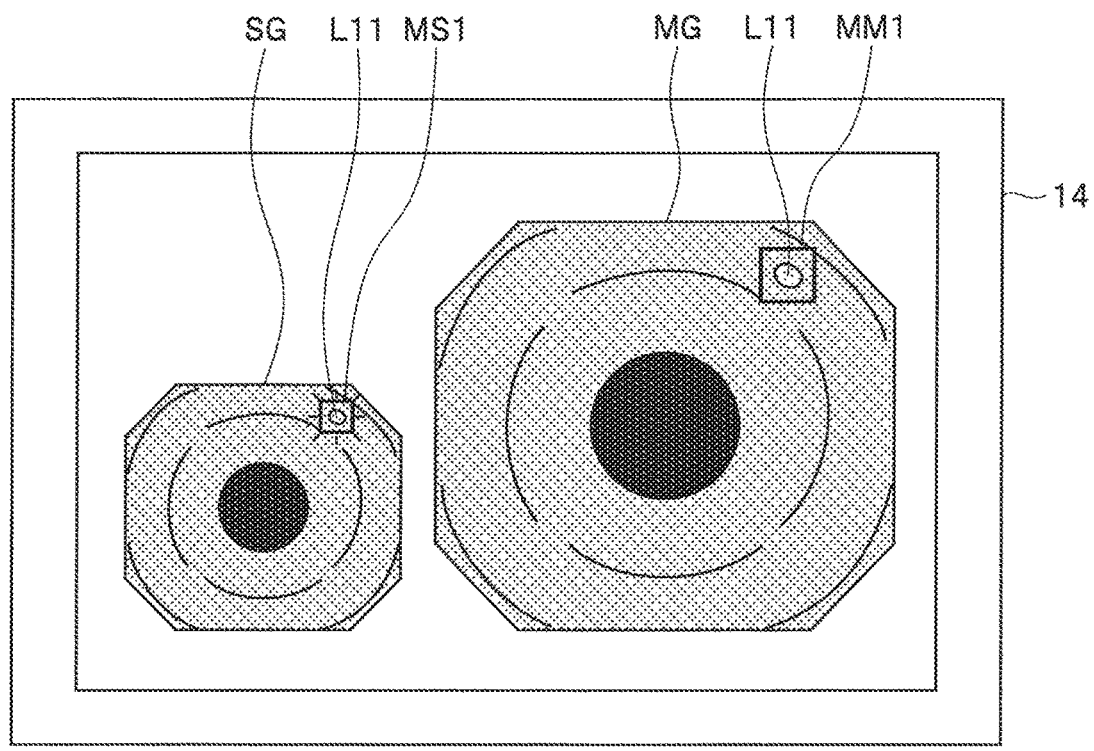
FIG. 5 is a diagram showing an example of a display image displayed according to the processing of the endoscopic image processing apparatus according to the first embodiment.

When the processing in step S16 is performed through the processing in step S14 in FIG. 3, for example, the display image shown in FIG. 4 or FIG. 5 is generated and the generated display image is displayed on the display apparatus 14. FIG. 4 and FIG. 5 are diagrams showing examples of display images displayed according to the processing of the endoscopic image processing apparatus according to the first embodiment.

In the display image illustrated in FIG. 4, the periphery of the lesion candidate region L11 included in the endoscopic image on the main screen MG is surrounded by the marker image MM1, which is a rectangular frame, and the periphery of the lesion candidate region L11 included in the endoscopic image on the sub-screen SG is surrounded by the marker image MS1, which is a rectangular frame. In the display image illustrated in FIG. 4, a frame line of the marker image MS1 is displayed at a line width larger than a line width of a frame line of the marker image MM1. Note that when the display image illustrated in FIG. 4 is displayed on the display apparatus 14, in step S14 in FIG. 3, the display control section 133 only has to perform processing for setting the line width of the frame line of the marker image MS1 corresponding to the highlighting level ES1 to a line width larger than the line width of the frame line of the marker image MM1 corresponding to the highlighting level EM1.

In the display image illustrated in FIG. 5, the periphery of the lesion candidate region L11 included in the endoscopic image on the main screen MG is surrounded by the marker image MM1 which is a rectangular frame, and the periphery of the lesion candidate region L11 included in the endoscopic image on the sub-screen SG is surrounded by the marker image MS1, which is a rectangular frame. In the display image illustrated in FIG. 5, a frame line of the marker image MS1 is displayed brighter than a frame line of the marker image MM1. Note that when the display image illustrated in FIG. 5 is displayed on the display apparatus 14, in step S14 in FIG. 3, the display control section 133 only has to perform processing for setting a brightness level of the frame line of the marker image MS1 corresponding to the highlighting level ES1 to a brightness level higher than a brightness level of the frame line of the marker image MM1 corresponding to the highlighting level EM1.

Figure 6:
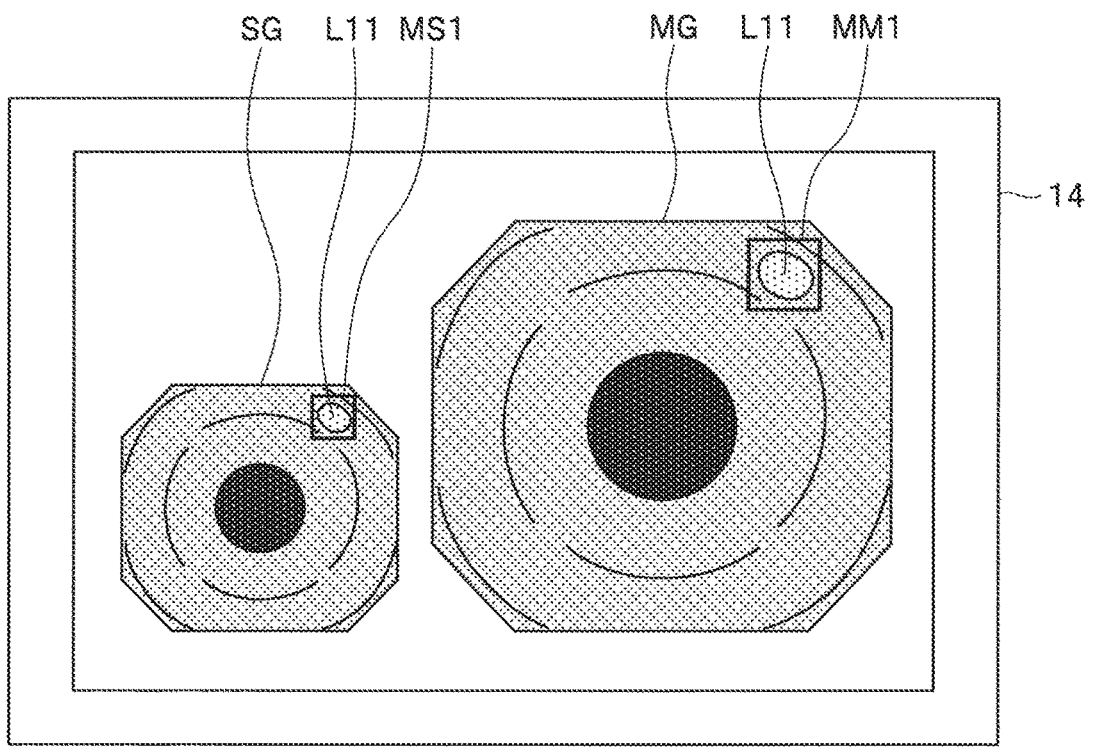
FIG. 6 is a diagram showing an example of a display image displayed according to the processing of the endoscopic image processing apparatus according to the first embodiment.

When the processing in S16 is performed through the processing in step S15 in FIG. 3, for example, the display image shown in FIG. 6 is generated and the generated display image is displayed on the display apparatus 14. FIG. 6 is a diagram showing an example of a display image displayed according to the processing of the endoscopic image processing apparatus according to the first embodiment.

In the display image illustrated in FIG. 6, the periphery of the lesion candidate region L11 included in the endoscopic image on the main screen MG is surrounded by the marker image MM1, which is a rectangular frame, and the periphery of the lesion candidate region L11 included in the endoscopic image on the sub-screen SG is surrounded by the marker image MS1, which is a rectangular frame. In the display image illustrated in FIG. 6, the marker images MM1 and MS1 are displayed in the same highlighted state.

As explained above, according to a series of processing shown in FIG. 3, a highlighted state of the marker image M added to the main screen MG is maintained irrespective of the difficulty in finding the lesion candidate region L included in endoscopic images simultaneously displayed on the main screen MG and the sub-screen SG. As explained above, according to the series of processing shown in FIG. 3, the highlighted state of the marker image M added to the sub-screen SG changes according to the difficulty in finding the lesion candidate region L included in the endoscopic images simultaneously displayed on the main screen MG and the sub-screen SG. Therefore, according to the present embodiment, it is possible to make it easy to confirm, on the sub-screen SG, a position of the lesion candidate region L having high difficulty of finding. Therefore it is possible to reduce a burden on a user who views endoscopic images simultaneously displayed on a plurality of screens and performs work.

Note that, according to the present embodiment, as long as processing for changing the highlighted state of the marker image MS1 added to the lesion candidate region L11 of the sub-screen SG according to the difficulty in finding the lesion candidate region L11 is performed, processing different from the processing explained above may be performed. More specifically, for example, when the evaluation result indicating that the difficulty in finding the lesion candidate region L11 is high is obtained, in step S14 in FIG. 3, processing relating to setting for flashing the marker image MS1 added to the lesion candidate region may be performed.

Second Embodiment

FIG. 7 to FIG. 10 relate to a second embodiment of the present invention.

Note that, in the present embodiment, detailed explanation concerning portions having the same components and the like as the components and the like in the first embodiment is omitted. Portions having components and the like different from the components and the like in the first embodiment are mainly explained.

The endoscopic image processing apparatus 13 in the present embodiment is configured to perform processing different from the processing explained in the first embodiment.

Figure 7:
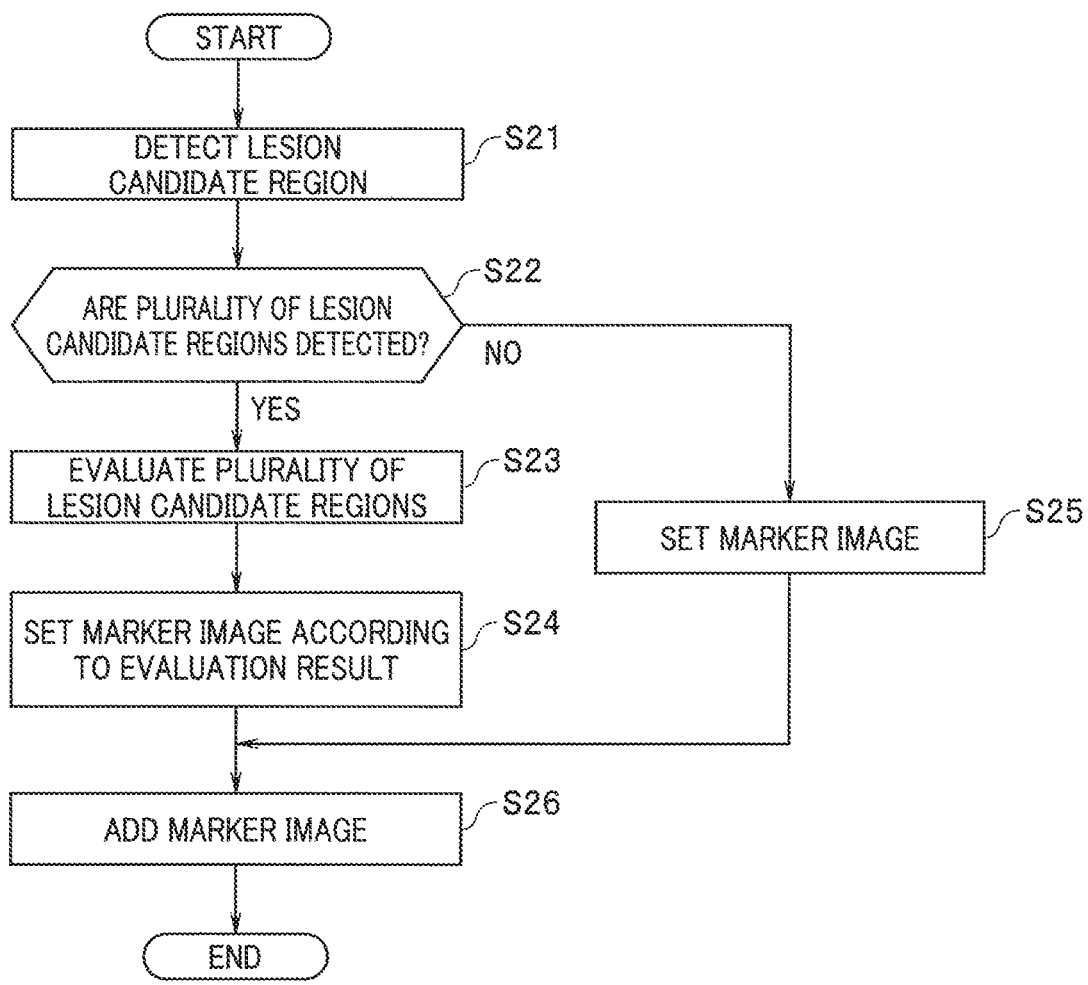
FIG. 7 is a flowchart for explaining a specific example of processing performed in an endoscopic image processing apparatus according to a second embodiment.

Specific examples of processing performed in sections of the endoscopic image processing apparatus 13 in the present embodiment are explained with reference to FIG. 7 and the like. FIG. 7 is a flowchart for explaining a specific example of processing performed in an endoscopic image processing apparatus according to the second embodiment.

The lesion-candidate-region detecting section 131 performs processing for detecting the lesion candidate region L included in an endoscopic image outputted from the main body apparatus 12 and performs processing for acquiring the lesion candidate information IL, which is information indicating the detected lesion candidate region L (step S21 in FIG. 7).

The lesion-candidate-region evaluating section 132 performs processing for determining Whether or not a plurality of lesion candidate regions L are detected by the processing in step S21 in FIG. 7 (step S22 in FIG. 7).

When obtaining a determination result indicating that a plurality of lesion candidate regions L are detected by the processing in step S21 in FIG. 7 (S22: YES), the lesion-candidate-region evaluating section 132 performs processing for evaluating the plurality of lesion candidate regions L (step S23 in FIG. 7).

Concerning a specific example of the processing performed in step S23 in FIG. 7, a case is explained, as an example, in which a lesion candidate region L21 and a lesion candidate region L22 are detected, lesion candidate information IL21 corresponding to the lesion candidate region L21 is acquired, and lesion candidate information IL22 corresponding to the lesion candidate region L22 is acquired by the processing in step S21 in FIG. 7.

For example, the lesion-candidate-region evaluating section 132 calculates a relative distance DA equivalent to a distance between centers of the lesion candidate regions L21 and L22 based on the lesion candidate information IL21 corresponding to the lesion candidate region L21 detected by the processing in step S21 in FIG. 7 and the lesion candidate information IL22 corresponding to the lesion candidate region L22 detected by the processing in step S21 in FIG. 7.

For example, the lesion-candidate-region evaluating section 132 compares the relative distance DA and a predetermined threshold THA to thereby evaluate a positional relation between the lesion candidate regions L21 and L22. For example, when obtaining a comparison result indicating DA≤THA, the lesion-candidate-region evaluating section 132 obtains an evaluation result indicating that the lesion candidate regions L21 and L22 are present in positions close to each other. For example, when obtaining a comparison result indicating DA>THA, the lesion-candidate-region evaluating section 132 obtains an evaluation result indicating that the lesion candidate regions L21 and L22 are present in positions far apart from each other.

In other words, according to the specific example explained above, the lesion-candidate-region evaluating section 132 performs processing for evaluating, based on a relative distance between the plurality of lesion candidate regions L (the lesion candidate regions L21 and L22) detected by the processing of the lesion-candidate-region detecting section 131, a positional relation between the plurality of lesion candidate regions L.

The lesion-candidate-region evaluating section 132 performs the same processing as the processing in step S12 in FIG. 3 based on at least one of the endoscopic image in which the lesion candidate region L21 is detected by the processing in step S21 in FIG. 7 or the lesion candidate information IL21 corresponding to the lesion candidate region L21 to thereby evaluate difficulty in finding the lesion candidate region L21. The lesion-candidate-region evaluating section 132 performs the same processing as the processing in step S12 in FIG. 3 based on at least one of the endoscopic image in which the lesion candidate region L22 is detected by the processing in step S21 in FIG. 7 or the lesion candidate information IL22 corresponding to the lesion candidate region L22 to thereby evaluate difficulty in finding the lesion candidate region L22. The lesion-candidate-region evaluating section 132 respectively acquires an evaluation result relating to the difficulty in finding the lesion candidate region L21 and an evaluation result relating to the difficulty in finding the lesion candidate region L22.

In other words, according to the specific example explained above, the lesion-candidate-region evaluating section 132 performs processing for evaluating the difficulty in finding each of the plurality of lesion candidate regions L (the lesion candidate regions L21 and L22) detected by the processing of the lesion-candidate-region detecting section 131.

When obtaining a determination result indicating that the plurality of lesion candidate regions L are detected by the processing in step S21 in FIG. 7 (S22: YES), the display control section 133 performs processing for setting, according to the evaluation result obtained by the processing in step S23 in FIG. 7, the marker image M added by highlighting processing of the highlighting processing section 133A (step S24 in FIG. 7).

A specific example of the processing performed in step S24 in FIG. 7 is explained.

For example, when an evaluation result indicating that the lesion candidate regions L21 and L22 are present in positions close to each other is obtained, the display control section 133 sets a marker image MM2 for collectively highlighting the positions of the lesion candidate regions L21 and L22 on the main screen MG and sets marker images MS21 and MS22 for individually highlighting the positions of the lesion candidate regions L21 and L22 on the sub-screen SG. For example, when an evaluation result indicating that the lesion candidate regions L21 and L22 are present in positions far apart from each other is obtained, the display control section 133 sets marker images MM21 and MM22 for individually highlighting the positions of the lesion candidate regions L21 and L22 on the main screen MG and sets the marker images MS21 and MS22 for individually highlighting the positions of the lesion candidate regions L21 and L22 on the sub-screen SG.

In other words, according to the specific example explained above, the display control section 133 sets, based on an evaluation result of a positional relation between the plurality of lesion candidate regions L (the lesion candidate regions L21 and L22) obtained by the processing of the lesion-candidate-region evaluating section 132, a highlighting method in highlighting, with the processing of the highlighting processing section 133A, positions of the plurality of lesion candidate regions L included in the main screen MG and the sub-screen SG. According to the specific example explained above, the display control section 133 performs setting for collectively highlighting, on the main screen MG, and individually highlighting, on the sub-screen SG, of the plurality of lesion candidate regions L (the lesion candidate regions L21 and L22) detected by the processing in the lesion-candidate-region detecting section 131, positions of the lesion candidate regions L where an evaluation result indicating that the lesion candidate regions L are present in positions close to each other is obtained by the processing of the lesion-candidate-region evaluating section 132. According to the specific example explained above, the display control section 133 performs setting for individually highlighting, on both of the main screen MG and the sub-screen SG, of the plurality of lesion candidate regions L (the lesion candidate regions L21 and L22) detected by the processing in the lesion-candidate-region detecting section 131, positions of the lesion candidate regions L where an evaluation result indicating that the lesion candidate regions L are present in positions farther apart from each other is obtained by the processing of the lesion-candidate-region evaluating section 132.

For example, when an evaluation result indicating that the difficulty in finding the lesion candidate region L21 is high is obtained, the display control section 133 respectively sets the marker image MM21 for highlighting the position of the lesion candidate region L21 on the main screen MG and the marker image MS21 for highlighting the position of the lesion candidate region L21 on the sub-screen SG. For example, when an evaluation result indicating that the difficulty in finding the lesion candidate region L21 is low is obtained, the display control section 133 sets the marker image MS21 for highlighting the position of the lesion candidate region L21 on the sub-screen SG.

For example, when an evaluation result indicating that the difficulty in finding the lesion candidate region L22 is high is obtained, the display control section 133 respectively sets the marker image MM22 for highlighting the position of the lesion candidate region L22 on the main screen MG and the marker image MS22 for highlighting the position of the lesion candidate region L22 on the sub-screen SG. For example, when an evaluation result indicating that the difficulty in finding the lesion candidate region L22 is low is obtained, the display control section 133 sets the marker image MS22 for highlighting the position of the lesion candidate region L22 on the sub-screen SG.

In other words, according to the specific example explained above, the display control section 133 performs setting for highlighting, on the main screen MG and the sub-screen SG, of the plurality of lesion candidate regions L (the lesion candidate regions L21 and L22) detected by the processing of the lesion-candidate-region detecting section 131, the position of the lesion candidate region L where an evaluation result indicating that the difficulty in finding the lesion candidate region L is high is obtained by the processing of the lesion-candidate-region evaluating section 132. According to the specific example explained above, the display control section 133 performs setting for highlighting, on the sub-screen SG, of the plurality of lesion candidate regions L (the lesion candidate regions L21 and L22) detected by the processing of the lesion-candidate-region detecting section 131, the position of the lesion candidate region L where an evaluation result indicating that the difficulty in finding the lesion candidate region L is low is obtained by the processing of the lesion-candidate-region evaluating section 132.

When obtaining a determination result indicating that one lesion candidate region L is detected by the processing in step S21 in FIG. 7 (S22: NO), the display control section 133 performs processing for setting the marker image M for highlighting a position of the one lesion candidate region L on each of the main screen MG and the sub-screen SG (step S25 in FIG. 7).

More specifically, for example, the display control section 133 respectively sets a marker image MM23 for highlighting, on the main screen MG, a position of a lesion candidate region L23 detected by the processing in step S21 in FIG. 7 and a marker image MS23 for highlighting the position of the lesion candidate region L23 on the sub-screen SG.

The highlighting processing section 133A performs processing for adding, based on the lesion candidate information IL acquired by the processing in step S21 in FIG. 7, the marker image M set through the processing in step S24 or step S25 in FIG. 7 (step S26 in FIG. 7).

Figure 8:
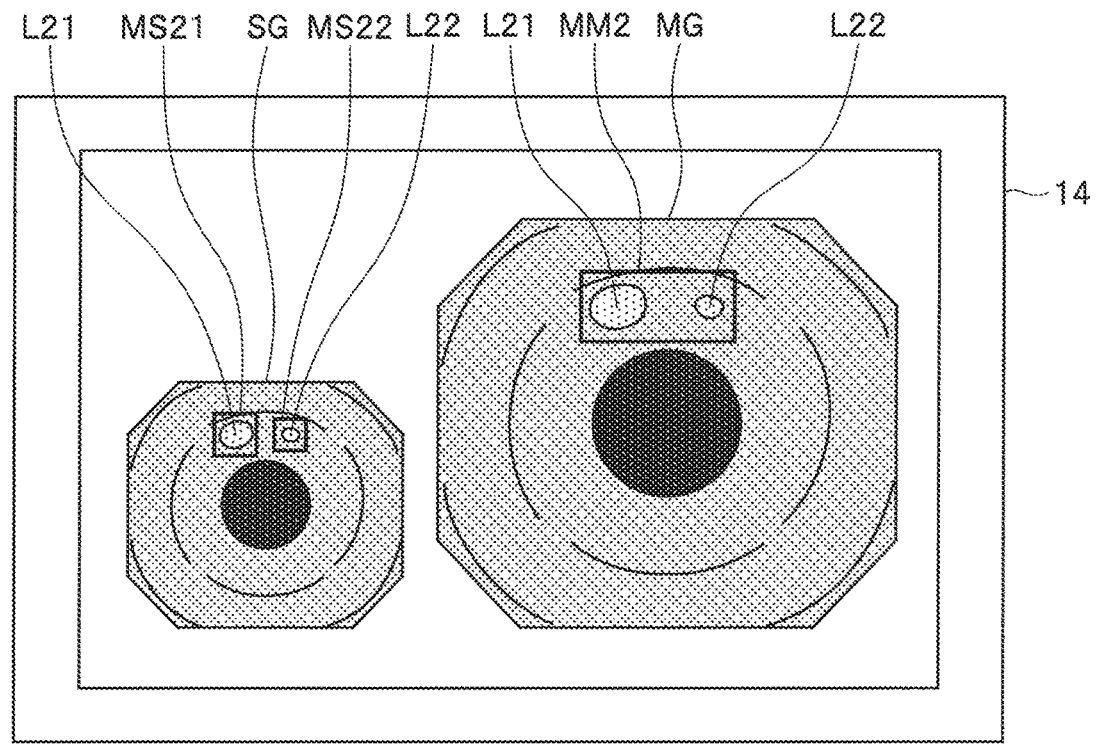
FIG. 8 is a diagram showing an example of a display image displayed according to the processing of the endoscopic image processing apparatus according to the second embodiment.
Figure 9:
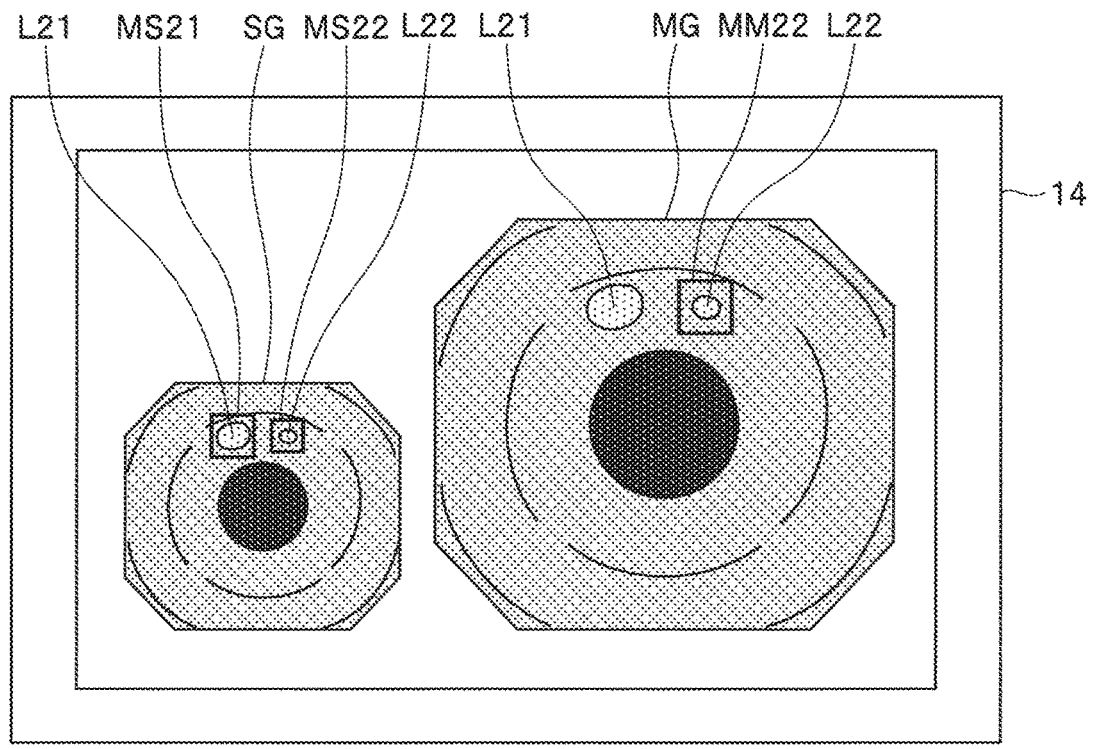
FIG. 9 is a diagram showing an example of a display image displayed according to the processing of the endoscopic image processing apparatus according to the second embodiment.

When the processing in step S26 is performed through the processing in step S24 in FIG. 7, for example, a display image shown in FIG. 8 or FIG. 9 is generated and the generated display image is displayed on the display apparatus 14. FIG. 8 and FIG. 9 are diagrams showing examples of display images displayed according to processing of the endoscopic image processing apparatus according to the second embodiment.

In the display image illustrated in FIG. 8, peripheries of the lesion candidate regions L21 and L22 included in the endoscopic image on the main screen MG are surrounded by the marker image MM2, which is a rectangular frame, a periphery of the lesion candidate region L21 included in the endoscopic image on the sub-screen SG is surrounded by the marker image MS21, which is a rectangular frame, and a periphery of the lesion candidate region L22 included in the endoscopic image on the sub-screen SG is surrounded by the marker image MS22, which is a rectangular frame. In other words, in a series of processing shown in FIG. 7, when an evaluation result indicating that the lesion candidate regions L21 and L22 are present in positions close to each other is obtained, the display image shown in FIG. 8 is displayed on the display apparatus 14.

In the display image illustrated in FIG. 9, the periphery of the lesion candidate region L22 included in the endoscopic image on the main screen MG is surrounded by the marker image MM22, which is a rectangular frame, the periphery of the lesion candidate region L21 included in the endoscopic image on the sub-screen SG is surrounded by the marker image MS21, which is a rectangular frame, and the periphery of the lesion candidate region L22 included in the endoscopic image on sub-screen SG is surrounded by the marker image MS22, which is a rectangular frame. In other words, in the series of processing shown in FIG. 7, when an evaluation result indicating that the difficulty in finding the lesion candidate region L21 is low is obtained because a size of the lesion candidate region L21 is larger than a predetermined size and an evaluation result indicating that the difficulty in finding the lesion candidate region L22 is high is obtained because a size of the lesion candidate region L22 is equal to or smaller than the predetermined size, the display image shown in FIG. 9 is displayed on the display apparatus 14.

Figure 10:
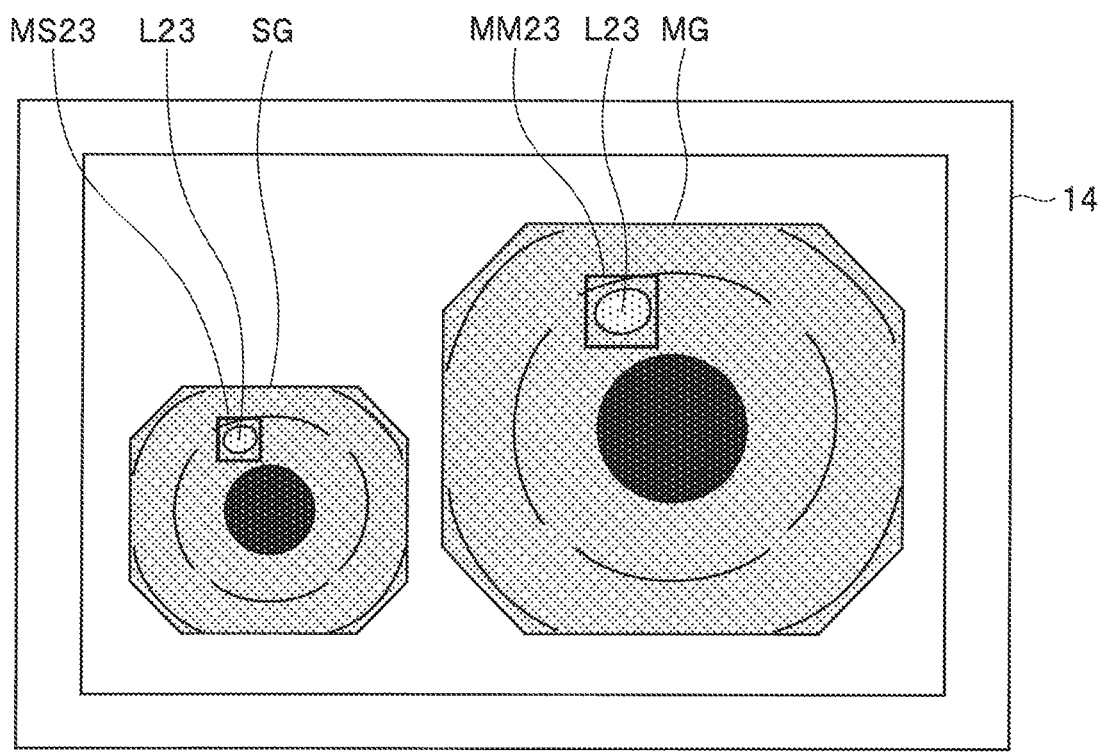
FIG. 10 is a diagram showing an example of a display image displayed according to the processing of the endoscopic image processing apparatus according to the second embodiment.

When the processing in step S26 is performed through the processing in step S25 in FIG. 7, for example, a display image shown in FIG. 10 is generated and the generated display image is displayed on the display apparatus 14. FIG. 10 is a diagram showing an example of a display image displayed according to the processing of the endoscopic image processing apparatus according to the second embodiment.

In the display image illustrated in FIG. 10, a periphery of the lesion candidate region L23 included in the endoscopic image on the main screen MG is surrounded by a marker image MM23, which is a rectangular frame, and a periphery of the lesion candidate region L23 included in the endoscopic image on the sub-screen SG is surrounded by a marker image MS23, which is a rectangular frame.

As explained above, according to the series of processing shown in FIG. 7, irrespective of the number of lesion candidate regions L included in endoscopic images simultaneously displayed on the main screen MG and the sub-screen SG, the marker image M is added to all the lesion candidate regions L included in the endoscopic image on the sub-screen SG. As explained above, according to the series of processing shown in FIG. 7, when one lesion candidate region L is included in the endoscopic images simultaneously displayed on the main screen MG and the sub-screen SG, the marker image M for highlighting a position of the one lesion candidate region L is added to the main screen. As explained above, according to the series of processing shown in FIG. 7, when a plurality of lesion candidate regions are included in the endoscopic images simultaneously displayed on the main screen MG and the sub-screen SG, a total number of marker images M simultaneously added to the main screen MG can be set to less than a total number of lesion candidate regions L detected from the endoscopic image. Therefore, according to the present embodiment, the marker image M can be added to the main screen MG not to hinder, as much as possible, work performed by viewing the main screen MG. Therefore, it is possible to reduce a burden on a user who views endoscopic images simultaneously displayed on a plurality of screens and performs work.

Third Embodiment

FIG. 11 to FIG. 14 relate to a third embodiment of the present invention.

Note that, in the present embodiment, detailed explanation concerning portions having the same components and the like as the components and the like in at least one of the first or second embodiment is omitted. Portions having components and the like different from the components and the like in both of the first and second embodiments are mainly explained.

Figure 11:
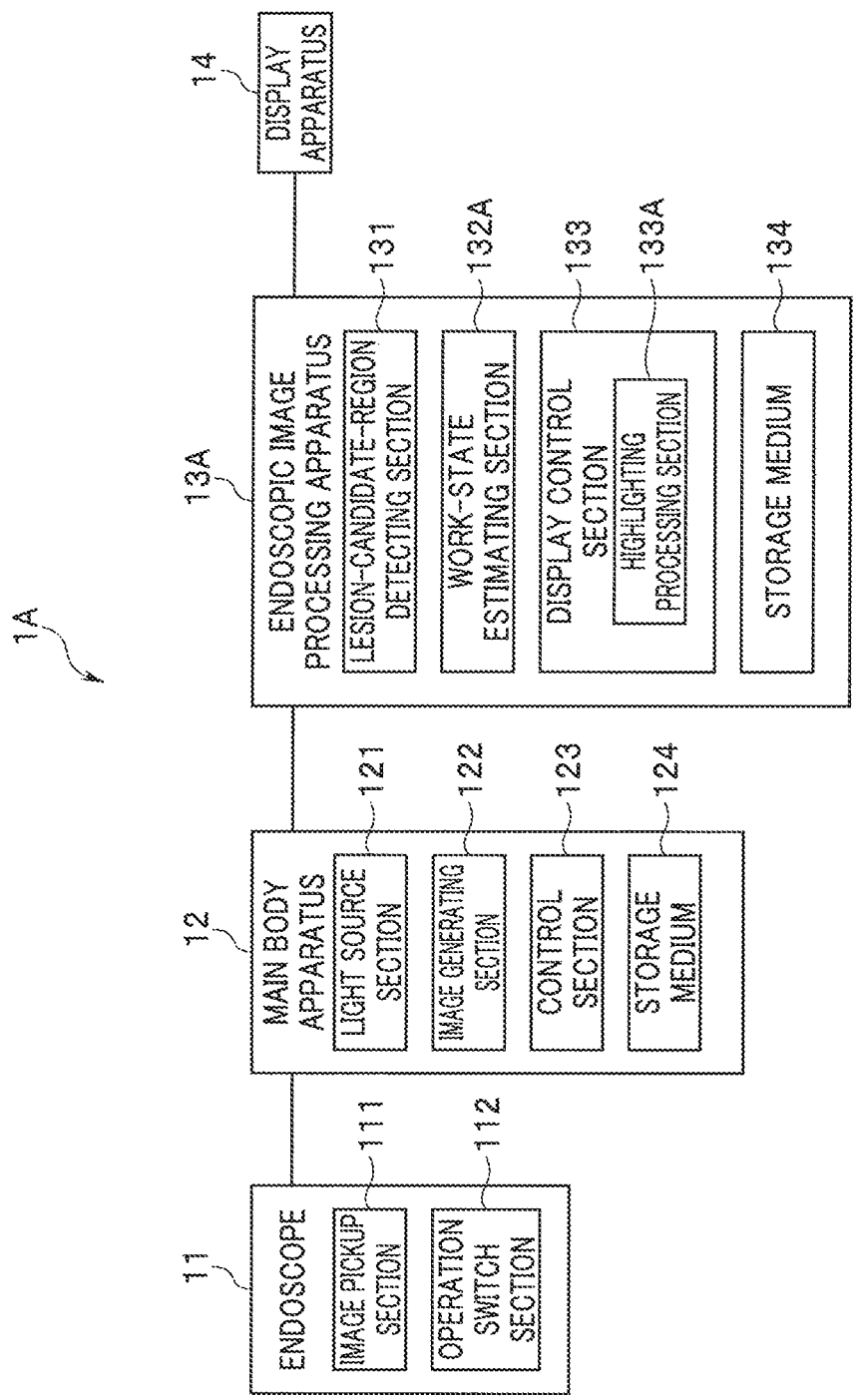
FIG. 11 is a diagram showing a configuration of a main part of an endoscope system including an endoscopic image processing apparatus according to a third embodiment.

As shown in FIG. 11, an endoscope system 1A is configured by providing an endoscopic image processing apparatus 13A instead of the endoscopic image processing apparatus 13 explained in the first embodiment. As shown in FIG. 11, the endoscopic image processing apparatus 13A is configured by providing a work-state estimating section 132A instead of the lesion-candidate-region evaluating section 132 explained in the first embodiment. FIG. 11 is a diagram showing a configuration of a main part of an endoscope system including an endoscopic image processing apparatus according to the third embodiment.

For example, the work-state estimating section 132A is configured to be able to detect an instruction given by the operation switch section 112 of the endoscope 11 by monitoring operation of the control section 123 of the main body apparatus 12. The work-state estimating section 132A is configured to perform processing for estimating, based on at least one of an endoscopic image outputted from the main body apparatus 12 or a detection result of the instruction given by the operation switch section 112, a work state of a user at the time when the lesion candidate region L is detected by the lesion-candidate-region detecting section 131. In other words, the work-state estimating section 132A is configured to perform processing for estimating, based on at least one of the endoscopic image outputted from the main body apparatus 12 or a detection result of an instruction given to set operation states of one or more functions of the endoscope 11, a work state of the user at the time when the lesion candidate region L is detected by the lesion-candidate-region detecting section 131.

Figure 12:
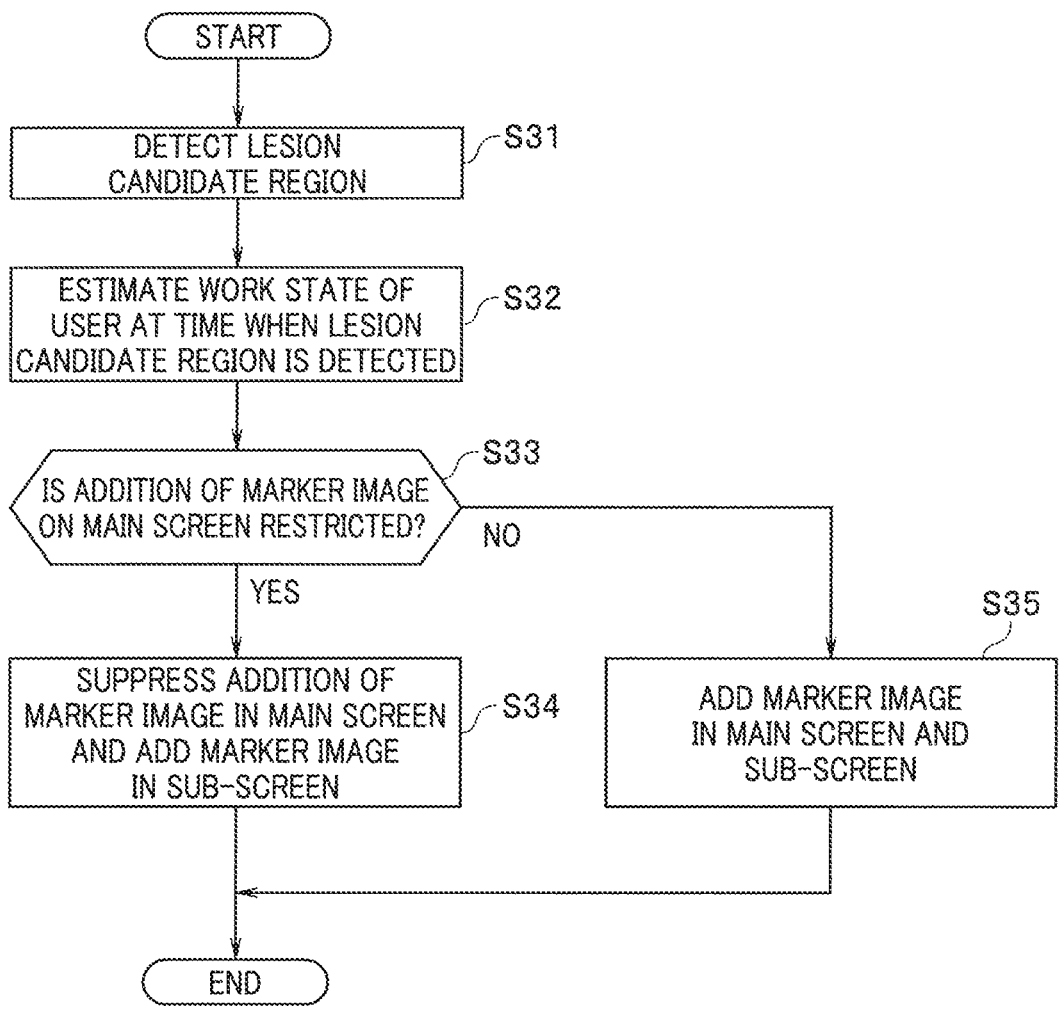
FIG. 12 is a flowchart for explaining a specific example of processing performed in the endoscopic image processing apparatus according to the third embodiment.

Specific examples of processing performed in sections of the endoscopic image processing apparatus 13A in the present embodiment are explained with reference to FIG. 12 and the like. Note that, in the present embodiment, a case is explained, as an example, in which one lesion candidate region L is included in the endoscopic image outputted from the main body apparatus 12. FIG. 12 is a flowchart for explaining a specific example of processing performed in the endoscopic image processing apparatus according to the third embodiment.

The lesion-candidate-region detecting section 131 performs processing for detecting the lesion candidate region L included in the endoscopic image outputted from the main body apparatus 12 and performs processing for acquiring the lesion candidate information IL, which is information indicating the detected lesion candidate region L (step S31 in FIG. 12).

More specifically, for example, the lesion-candidate-region detecting section 131 performs the processing in step S31 in FIG. 12 to thereby detect a lesion candidate region L31 included in the endoscopic image outputted from the main body apparatus 12 and acquire lesion candidate information IL31, which is information indicating the detected lesion candidate region L31.

The work-state estimating section 132A performs processing for estimating, based on at least one of the endoscopic image outputted from the main body apparatus 12 or a detection result of the instruction given by the operation switch section 112, a work state of the user at the time when the lesion candidate region L is detected by the processing in step S31 in FIG. 12 (step S32 in FIG. 12).

A specific example of the processing performed in step S32 in FIG. 12 is explained.

The work-state estimating section 132A performs processing for calculating a motion vector of endoscopic images of a plurality of frames sequentially outputted from the main body apparatus 12. For example, when a motion vector calculated when the lesion candidate region L31 is detected by the processing in step S31 in FIG. 12 is directed to a dark side (a depth side) of the endoscopic image and the work-state estimating section 132A detects that a size of the motion vector is equal to or larger than a predetermined threshold THV, the work-state estimating section 132A obtains an estimation result indicating that work relating to insertion of (the insertion section of) the endoscope 11 is performed. For example, when detecting that the motion vector calculated when the lesion candidate region L31 is detected by the processing in step S31 in FIG. 12 is not directed to the dark side (the depth side) of the endoscopic image or when detecting that the size of the motion vector is smaller than the predetermined threshold THV, the work-state estimating section 132A determines that work different from the work relating to the insertion of (the insertion section of) the endoscope 11 is performed.

For example, the work-state estimating section 132A performs image recognition processing on the endoscopic images sequentially outputted from the main body apparatus 12 to thereby obtain a processing result relating to which part in a large intestine of a human body a part, an image of which is picked up by the endoscope 11, corresponds and perform, according to the processing result, setting of a flag FC indicating whether the endoscope 11 has reached an appendix. For example, the flag FC is set to off when a power supply of the endoscopic image processing apparatus 13A is turned on and is set to on when a processing result indicating that the part, the image of which is picked up by the endoscope 11, is the appendix is obtained first after the power supply of the endoscopic image processing apparatus 13A is turned on. When the flag FC at the time when the lesion candidate region L31 is detected by the processing in step S31 in FIG. 12 is off, the work-state estimating section 132A obtains an estimation result indicating that the work relating to the insertion of (the insertion section of) the endoscope 11 is performed. When the flag FC at the time when the lesion candidate region L31 is detected by the processing in step S31 in FIG. 12 is on, the work-state estimating section 132A determines that work different from the work relating to the insertion of (the insertion section of) the endoscope 11 is performed.

When determining that work different from the work relating to the insertion of (the insertion section of) the endoscope 11 is performed, for example, the work-state estimating section 132A specifies, based on a detection result of the instruction given by the operation switch section 112, observation magnification of the endoscope 11 (the image pickup section 111) at the time when the lesion candidate region L31 is detected by the processing in step S31 in FIG. 12. When the observation magnification of the endoscope 11 (the image pickup section 111) at the time when the lesion candidate region L31 is detected by the processing in step S31 in FIG. 12 is equal to or larger than a predetermined threshold THM, the work-state estimating section 132A obtains an estimation result indicating that work relating to a diagnosis of the lesion candidate region L is performed.

When determining that work different from the work relating to the insertion of (the insertion section of) the endoscope 11 is performed, for example, the work-state estimating section 132A specifies, based on the endoscopic image outputted from the main body apparatus 12, whether a distal end portion of a treatment instrument used for treatment for the lesion candidate region L31 detected by the processing in step S31 in FIG. 12 is included in the endoscopic image. When the distal end portion of the treatment instrument used for the treatment for the lesion candidate region L31 detected by the processing in step S31 in FIG. 12 is included in the endoscopic image, the work-state estimating section 132A obtains an estimation result indicating that work relating to the treatment of the lesion candidate region L is performed.

When determining that the work does not correspond to none of the work relating to the insertion of (the insertion section of) the endoscope 11, work relating to a diagnosis of the lesion candidate region L31 detected by the processing in step S31 in FIG. 12, and work relating to the treatment for the lesion candidate region L31, the work-state estimating section 132A obtains an estimation result indicating that work relating to a search for the lesion candidate region L31 is performed.

The display control section 133 performs processing for setting, based on the estimation result obtained by the processing in step S32 in FIG. 12, whether addition of the marker image M on the main screen MG is restricted (step S33 in FIG. 12). In other words, in step S33 in FIG. 12, the display control section 133 performs processing for setting, based on the estimation result of the work state of the user obtained by the processing of the work-state estimating section 132A, a highlighting method in highlighting, with the processing of the highlighting processing section 133A, positions of the lesion candidate region L included in the main screen MG and the sub-screen SG.

More specifically, for example, when any one of the estimation result indicating that the work relating to the insertion of (the insertion section of) the endoscope 11 is performed, the estimation result indicating that the work relating to the diagnosis of the lesion candidate region L31 detected by the processing in step S31 in FIG. 12 is performed, or the estimation result indicating that the work relating to the treatment for the lesion candidate region L31 is performed is obtained by the processing in step S32 in FIG. 12, the display control section 133 performs setting for restricting the addition of the marker image M on the main screen MG. For example, when the estimation result indicating that the work relating to the search for the lesion candidate region L31 detected by the processing in step S31 in FIG. 12 is performed is obtained by the processing in step S32 in FIG. 12, the display control section 133 performs setting for not restricting the addition of the marker image M on the main screen MG.

In other words, according to the specific example explained above, when any one of the estimation result indicating that the work relating to the insertion of the endoscope 11 is performed, the estimation result indicating that the work relating to the diagnosis of the lesion candidate region L detected by the lesion-candidate-region detecting section 131 is performed, or the estimation result indicating that the work relating to the treatment of the lesion candidate region L detected by the lesion-candidate-region detecting section 131 is performed is obtained by the processing of the work-state estimating section 132A, the display control section 133 performs setting for restricting the processing of the highlighting processing section 133A for the main screen MG.

The highlighting processing section 133A performs processing for suppressing addition of the marker image M on an inside of the main screen MG and adding the marker image M to an inside of the sub-screen SG based on the lesion candidate information IL31 acquired by the processing in step S31 in FIG. 12 and a setting content set by the processing in step S33 in FIG. 12 (step S34 in FIG. 12).

Figure 13:
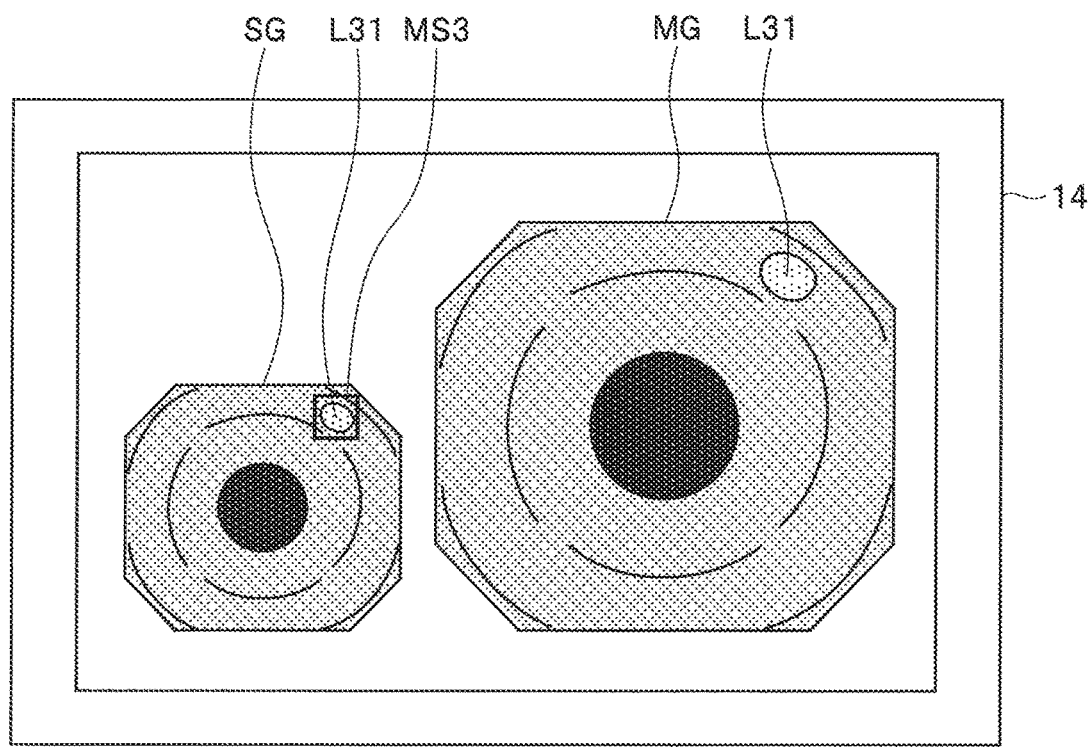
FIG. 13 is a diagram showing an example of a display image displayed according to the processing of the endoscopic image processing apparatus according to the third embodiment.
Figure 14:
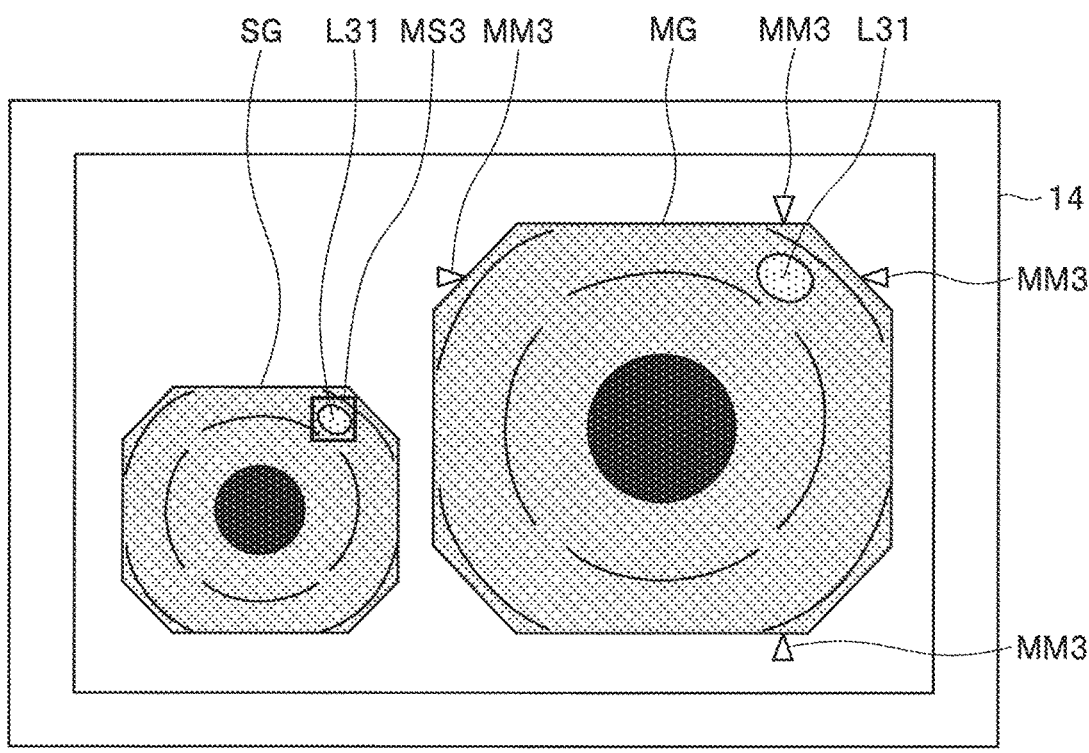
FIG. 14 is a diagram showing an example of a display image displayed according to the processing of the endoscopic image processing apparatus according to the third embodiment.

When the processing in step S34 in FIG. 12 is performed, for example, a display image shown in FIG. 13 or FIG. 14 is generated and the generated display image is displayed on the display apparatus 14. FIG. 13 and FIG. 14 are diagrams showing examples of display images displayed according to processing of the endoscopic image processing apparatus according to the third embodiment.

In the display image illustrated in FIG. 13, a periphery of the lesion candidate region L31 included in an endoscopic image on the sub-screen SG is surrounded by a marker image MS3 which is a rectangular frame, and, on the other hand, the marker image M is not added to a periphery of the lesion candidate region L31 included in an endoscopic image on the main screen MG. In other words, when the processing for not adding the marker image M to the main screen MG and for adding the marker image M to the inside of the sub-screen SG is performed in step S34 in FIG. 12, the display image illustrated in FIG. 13 is displayed on the display apparatus 14. Further, in other words, when processing for not highlighting a position of the legion candidate region L included in the main screen MG and for highlighting a position of the lesion candidate region L included in the sub-screen SG is performed by the highlighting processing section 133A based on the setting content set by the processing of the display control section 133 in step S34 in FIG. 12, the display image illustrate in FIG. 13 is displayed on the display apparatus 14.

In the display image illustrated in FIG. 14, the periphery of the lesion candidate region L31 included in the endoscopic image on the sub-screen SG is surrounded by the marker image MS3, which is a rectangular frame, and one marker image MM3, which is a triangular mark for pointing a position of the lesion candidate region L31 included in the endoscopic image on the main screen MG, is added to each of a top, a bottom, left, and right on an outside of the main screen MG. In other words, when processing for adding the marker image M to the outside of the main screen MG is performed and processing for adding the marker image M to the inside of the sub-screen SG is performed in step S34 in FIG. 12, the display image illustrated in FIG. 14 is displayed on the display apparatus 14. Further, in other words, when processing for highlighting, on the outside of the main screen MG, the position of the lesion candidate region L included in the main screen MG is performed and processing for highlighting, on the inside of the sub-screen SG, the position of the lesion candidate region L included in the sub-screen SG is performed by the highlighting processing section 133A based on the setting content set by the processing of the display control section 133 in step S34 in FIG. 12, the display image illustrated in FIG. 14 is displayed on the display apparatus 14.

The highlighting processing section 133A performs processing for adding the marker images M respectively to the inside of the main screen MG and the inside of the sub-screen SG based on the lesion candidate information IL acquired by the processing in step S31 in FIG. 12 and the setting content set by the processing in step S33 in FIG. 12 (step S35 in FIG. 12).

When the processing in step S35 in FIG. 12 is performed, for example, a display image substantially the same as the display image shown in FIG. 6 is displayed on the display apparatus 14.

As explained above, according to a series of processing shown in FIG. 12, for example, when endoscopic images are simultaneously displayed on the main screen MG and the sub-screen SG and, at the same time, work in which a time period for gazing the main screen MG is sufficiently longer than a time period for gazing the sub-screen SG is performed, it is possible to restrict addition of the marker image M to the lesion candidate region L included in the main screen MG not to hinder the work. Therefore, according to the present embodiment, it is possible to reduce a burden on a user who views endoscopic images simultaneously displayed on a plurality of screens and performs work.

Note that, in the present embodiment, for example, when an LED that generates NB light, which is blue narrow-band light, a center wavelength of which is set to near 415 nm, and an LED that generates NG light, which is green narrow-band light, a center wavelength of which is set to near 540 nm, are further provided in the light source section 121, in step S32 in FIG. 12, processing for estimating a work state of the user may be performed based on the detection result of the instruction relating to the setting of an observation mode given by the operation switch section 112. More specifically, when detecting that an instruction for setting the observation mode to a white light observation mode, which is a mode for irradiating the B light, the G light, and the R light on an object and performing observation, is given, the work-state estimating section 132A may obtain an estimation result indicating that the work relating to the search for the lesion candidate region L is performed. For example, when detecting that an instruction for setting the observation mode to a narrow-band light observation mode, which is a mode for irradiating the NB light and the NG light on the object and performing observation, is given, the work-state estimating section 132A may obtain an estimation result indicating that the work relating to the diagnosis of the lesion candidate region L is performed.

Fourth Embodiment

FIG. 15 to FIG. 18 relate to a fourth embodiment of the present invention.

Note that, in the present embodiment, detailed explanation concerning portions having the same components and the like as the components and the like in at least any one of the first to third embodiments is omitted. Portions having components and the like different from the components and the like in all of the first to third embodiments are mainly explained.

Figure 15:
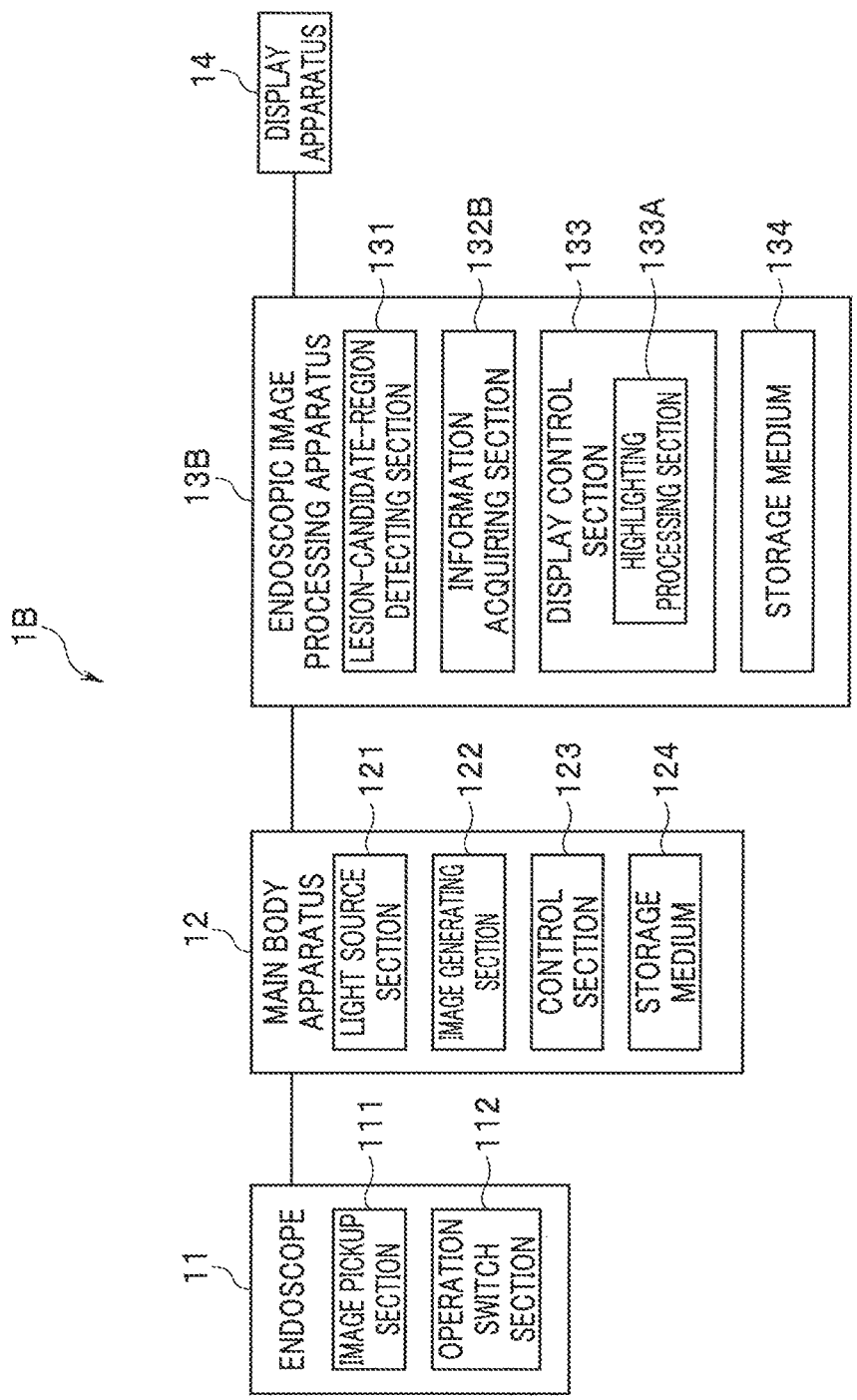
FIG. 15 is a diagram showing a configuration of a main part of an endoscope system including an endoscopic image processing apparatus according to a fourth embodiment.

As shown in FIG. 15, an endoscope system 1B is configured by providing an endoscopic image processing apparatus 13B instead of the endoscopic image processing apparatus 13 explained in the first embodiment. As shown in FIG. 15, the endoscopic image processing apparatus 13B is configured by providing an information acquiring section 132B instead of the lesion-candidate-region evaluating section 132 explained in the first embodiment. FIG. 15 is a diagram showing a configuration of a main part of an endoscope system including an endoscopic image processing apparatus according to the fourth embodiment.

The information acquiring section 132B is configured to, when the lesion candidate region L is detected by the lesion-candidate-region detecting section 131, perform processing for reading display setting information stored in the storage medium 134 and acquiring a setting value included in the read display setting information. In other words, the information acquiring section 132B is configured to acquire information relating to a display state at the time when a display image including the main screen MG and the sub-screen SG is displayed on the display apparatus 14.

Figure 16:
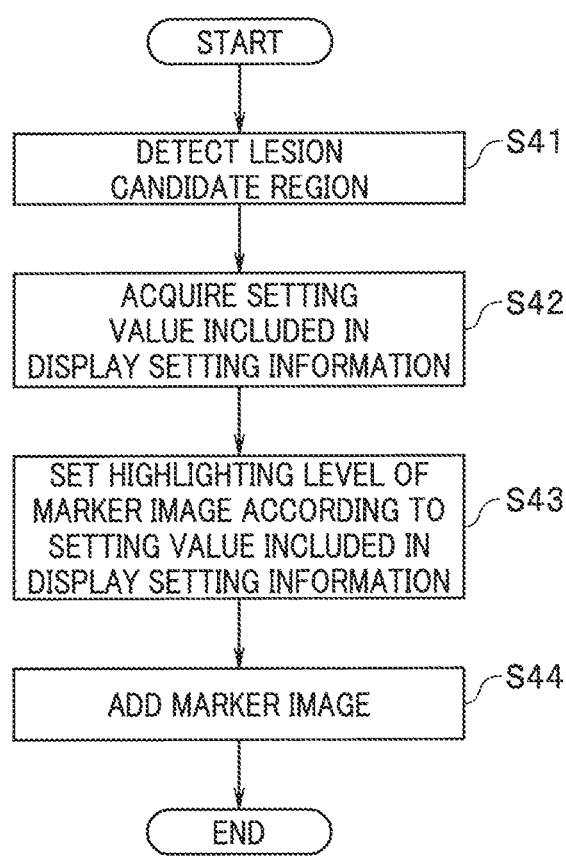
FIG. 16 is a flowchart for explaining a specific example of processing performed in the endoscopic image processing apparatus according to the fourth embodiment.

Specific examples of processing performed in sections of the endoscopic image processing apparatus 13B in the present embodiment are explained with reference to FIG. 16 and the like. Note that, in the present embodiment, a case is explained, as an example, in which one lesion candidate region L is included in an endoscopic image outputted from the main body apparatus 12. In the present embodiment, explanation is made assuming that it is possible to give, with operation of the operation switch section 112, an instruction for changing the setting value SS of a screen size of the sub-screen SG to a desired setting value within a range of a lower limit value Smin or more and an upper limit value Smax or less. In the present embodiment, explanation is made assuming that it is possible to give, with operation of the operation switch section 112, an instruction for changing the setting value BS of brightness of the entire display image including the main screen MG and the sub-screen SG to a desired setting value within a range of a lower limit value Bmin or more and an upper limit value Bmax or less. FIG. 16 is a flowchart for explaining a specific example of processing performed in the endoscopic image processing apparatus according to the fourth embodiment.

The lesion-candidate-region detecting section 131 performs processing for detecting the lesion candidate region L included in an endoscopic image outputted from the main body apparatus 12 and performs processing for acquiring the lesion candidate information IL, which is information indicating the detected lesion candidate region L (step S41 in FIG. 16).

More specifically, for example, the lesion-candidate-region detecting section 131 performs the processing in step S41 in FIG. 16 to thereby detect a lesion candidate region L41 included in the endoscopic image outputted from the main body apparatus 12 and acquire lesion candidate information IL41, which is information indicating the detected lesion candidate region L41.

When the lesion candidate region L is detected by the processing in step S41 in FIG. 16, the information acquiring section 132B performs processing for reading display setting information stored in the storage medium 134 and acquiring a setting value included in the read display setting information (step S42 in FIG. 16).

The display control section 133 performs processing for setting a highlighting level EM4 of a marker image MM4 added to the main screen MG to a predetermined highlighting level. The display control section 133 performs processing for setting, according to the setting value included in the display setting information acquired by the processing in step S42 in FIG. 16, a highlighting level ES4 of a marker image MS4 added to the sub-screen SG (step S43 in FIG. 16). In other words, the display control section 133 performs processing for setting a highlighting level in highlighting a position of the lesion candidate region L included in the main screen MG to a predetermined highlighting level and performs processing for changing, according to information acquired by the information acquiring section 132B, a highlighting level in highlighting a position of the lesion candidate region L included in the sub-screen SG.

A specific example of the processing performed in step S43 in FIG. 16 is explained.

For example, the display control section 133 performs setting for increasing the highlighting level ES4 of the marker image MS4 added to the sub-screen SG as the setting value SS of the screen size of the sub-screen SG included in the display setting information acquired by the processing in step S42 in FIG. 16 becomes closer to the lower limit value Smin. For example, the display control section 133 performs setting for reducing the highlighting level ES4 of the marker image MS4 added to the sub-screen SG as the setting value SS of the screen size of the sub-screen SG included in the display setting information acquired by the processing in step S42 in FIG. 16 becomes closer to the upper limit value Smax. In other words, in such a case, the display control section 133 performs setting for increasing the highlighting level ES4 of the marker image MS4 added to the sub-screen SG as the setting value SS of the screen size of the sub-screen SG decreases and reducing the highlighting level ES4 as the setting value SS increases.

For example, the display control section 133 performs setting for increasing the highlighting level ES4 of the marker image MS4 added to the sub-screen SG as the setting value BS of the brightness of the entire display image included in the display setting information acquired by the processing in step S42 in FIG. 16 becomes closer to the lower limit value Bmin. For example, the display control section 133 performs setting for reducing the highlighting level ES4 of the marker image MS4 added to the sub-screen SG as the setting value BS of the brightness of the entire display image included in the display setting information acquired by the processing in step S42 in FIG. 16 becomes closer to the upper limit value Bmax. In other words, in such a case, the display control section 133 performs setting for increasing the highlighting level ES4 of the marker image MS4 added to the sub-screen SG as the setting value BS of the brightness of the entire display image decreases and reducing the highlighting level ES4 as the setting value BS increases.

The highlighting processing section 133A performs processing for adding the marker image M to the main screen MG and the sub-screen SG based on the lesion candidate information IL41 acquired by the processing in step S41 in FIG. 16 and a setting content set by the processing in step S43 in FIG. 16 (step S44 in FIG. 16).

Figure 17:
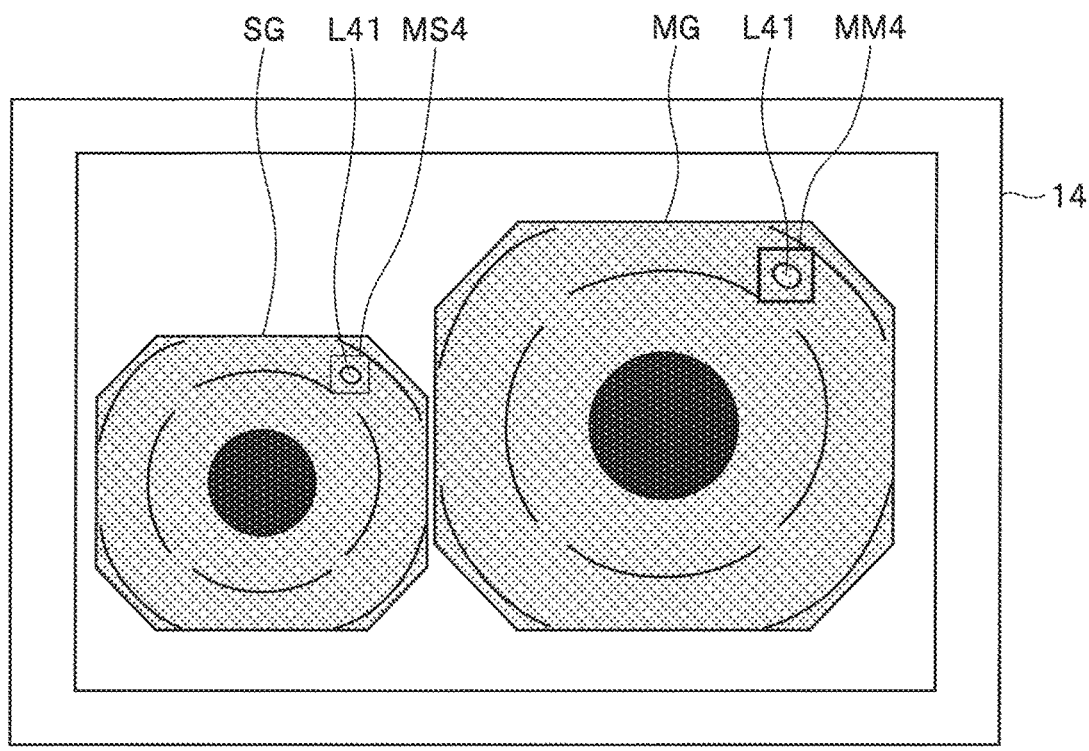
FIG. 17 is a diagram showing an example of a display image displayed according to the processing of the endoscopic image processing apparatus according to the fourth embodiment.
Figure 18:
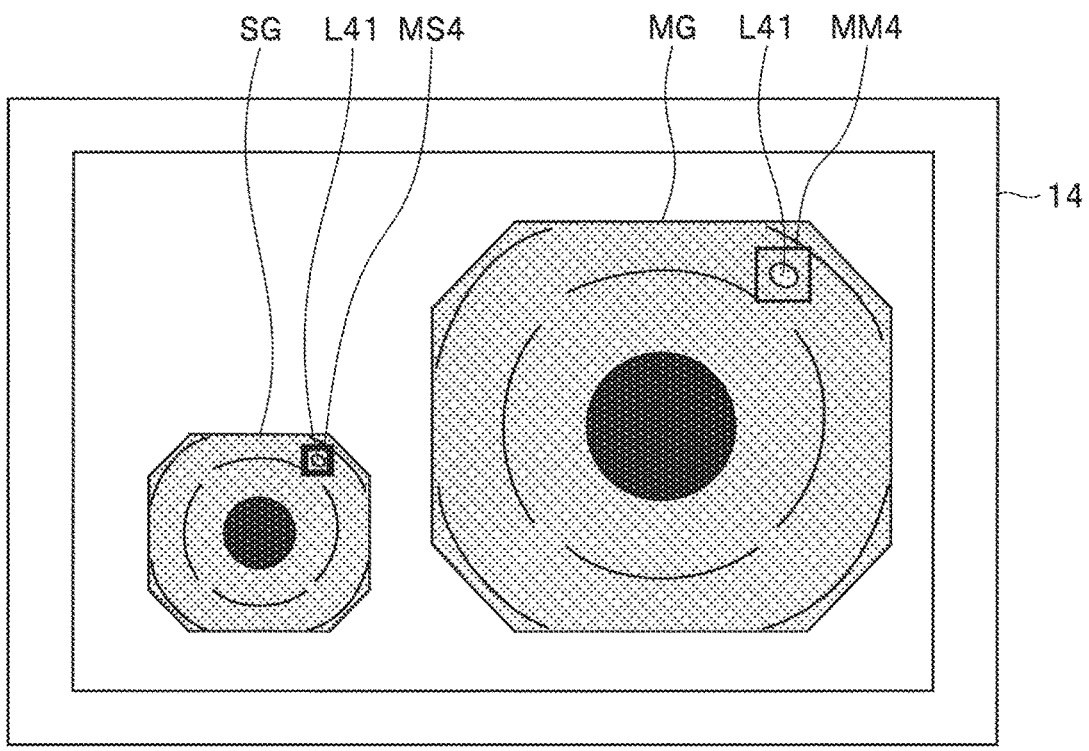
FIG. 18 is a diagram showing an example of a display image displayed according to the processing of the endoscopic image processing apparatus according to the fourth embodiment.

According to the processing in step S44 in FIG. 16, for example, a display image shown in FIG. 17 or FIG. 18 is generated and the generated display image is displayed on the display apparatus 14. FIG. 17 and FIG. 18 are diagrams showing an example of a display image displayed according to processing of the endoscopic image processing apparatus according to the fourth embodiment.

In the display image illustrated in FIG. 17, a periphery of the lesion candidate region L41 included in an endoscopic image on the main screen MG is surrounded by the marker image MM4, which is a rectangular frame, and a periphery of the lesion candidate region L41 included in an endoscopic image on the sub-screen SG is surrounded by the marker image MS4, which is a rectangular frame. In the display image illustrated in FIG. 17, the setting value SS of the screen size of the sub-screen SG is set to the upper limit value Smax (or a value close to the upper limit value Smax) and a frame line of the marker image MS4 is displayed as a line having small width equivalent to line width corresponding to the highlighting level ES4.

In the display image illustrated in FIG. 18, the periphery of the lesion candidate region L41 included in the endoscopic image on the main screen MG is surrounded by the marker image MM4, which is a rectangular frame, and the periphery of the lesion candidate region L41 included in the endoscopic image on the sub-screen SG is surrounded by the marker image MS4, which is a rectangular frame. In the display image illustrated in FIG. 18, the setting value SS of the screen size of the sub-screen SG is set to the lower limit value Smin (or a value close to the lower limit value Smin) and the frame line of the marker image MS4 is displayed as a line having large width equivalent to the line width corresponding to the highlighting level ES4.

As explained above, according to a series of processing shown in FIG. 16, for example, when endoscopic images are simultaneously displayed on the main screen MG and the sub-screen SG and, at the same time, the sub-screen SG is viewed and work relating to a diagnosis of the lesion candidate region L is performed, it is possible to change a highlighted state of the marker image M added to the sub-screen SG not to hinder the work. As explained above, according to the series of processing shown in FIG. 16, for example, when endoscopic images are simultaneously displayed on the main screen MG and the sub-screen SG and, at the same time, the main screen MG is viewed and work relating to a search for the lesion candidate region L is performed, even if a display state of the sub-screen SG is a state unsuitable for the work, it is possible to add the marker image M capable of supporting the work to the sub-screen SG. Therefore, according to the present embodiment, it is possible to reduce a burden on a user who views endoscopic images simultaneously displayed on a plurality of screens and performs work.

Note that, according to the present embodiment, for example, in step S43 in FIG. 16, processing for changing the highlighting level ES4 of the marker image MS4 added to the sub-screen SG may be performed according to a detection result of brightness of the endoscopic image outputted from the main body apparatus 12. More specifically, for example, in step S43 in FIG. 16, brightness of the endoscopic image outputted from the main body apparatus 12 may be detected and setting for increasing the highlighting level ES4 of the marker image MS4 added to the sub-screen SG as the detected brightness decreases and reducing the highlighting level ES4 as the detected brightness increases may be performed.

In the embodiments explained above, for example, a marker image MM added to the main screen MG and a marker image MS added to the sub-screen SG may be individually set to display or non-display according to an instruction given by an input apparatus such as the operation switch section 112. Note that, as the input apparatus, besides the operation switch section 112, for example, a footswitch, a keyboard, a tablet terminal, and a microphone and the like can be used.

The present invention is not limited to the embodiments explained above. It goes without saying that various changes and applications are possible within a range not departing from the gist of the invention.

What is claimed is:

1. An endoscopic image processing apparatus comprising:
at least one processor comprising hardware, the at least one processor being configured to:
generate a main image based on an endoscopic image;
generate a sub-image based on the endoscopic image, the sub-image being a copy of the main image;
using image processing of one or more candidate regions in the endoscopic image, determine a first marker of the main image and a second marker of the sub-image;
generate a user interface having an image including the main image and the sub-image, the first marker overlaid on the main image to indicate the one or more candidate regions in the main image and the second marker overlaid on the sub-image to indicate the one or more candidate regions in the sub-image, wherein the second marker is different from the first marker; and
display the user interface on a display.

2. The endoscopic image processing apparatus according to claim 1, wherein the image processing of the one or more candidate regions in the endoscopic image comprises:
determining a metric indicating how likely an observer of the endoscopic image would find the one or more candidate regions in the endoscopic image if not indicated;
determining whether the metric is more or less than a predetermined threshold; and
determining whether to change the second marker to differ from the first marker based on whether the metric is more or less than the predetermined threshold.

3. The endoscopic image processing apparatus according to claim 1, wherein the processor is configured to:
determine whether a distance between the one or more candidate regions is smaller than a predetermined distance;
when the distance is determined to be smaller than the predetermined distance, cause the first marker of the main image to collectively indicate positions of the one or more candidate regions and cause the second marker of the sub-image to individually indicate the positions, and
when the distance is determined to be larger than the predetermined distance, cause the first marker of the main image to individually indicate the positions, and cause the second marker of the sub-image to individually indicate the positions.

4. The endoscopic image processing apparatus according to claim 1, wherein the processor is configured to:
estimate a work state based on at least one of the endoscopic image or an instruction from a user; and
determine the marker and the second marker based on the estimated work state.

5. The endoscopic image processing apparatus according to claim 4, wherein the one or more candidate regions comprise one or more lesion candidate regions, and the processor is configured to restrict the overlaying of the first marker in the main image in the display image, when the estimated work state is related to one of insertion of the endoscope, a diagnosis of the one or more lesion candidate regions, or treatment of the one or more lesion candidate regions.

6. The endoscopic image processing apparatus according to claim 5, wherein in the display image, the first marker is not included on the main image in the display image and the second marker is on the sub-image, when the estimated work state is related to one of the insertion of the endoscope, the diagnosis of the one or more lesion candidate regions, or the treatment of the one or more lesion candidate regions.

7. The endoscopic image processing apparatus according to claim 6, wherein in the display image, the first marker is on an outside of the main image to indicate a first position of one or more lesion candidate regions included in the main image, and the second marker is on an inside of the sub-image to indicate a second position of the one or more lesion candidate regions included in the sub-image.

8. The endoscopic image processing apparatus according to claim 1, wherein the processor is configured to:
   acquire information relating to a display state at a time when the display image is displayed on the display; and
   determine the first marker and the second marker based on the acquired information.

9. The endoscopic image processing apparatus according to claim 8, wherein the acquired information is related to an image size of the sub-image in the display image, and
   the processor is configured to:
      increase an indicating level of a second indicating characteristic of the second marker in the sub-image as the image size of the sub-image becomes closer to a lower limit value; and
      reduce the indicating level of the second indicating characteristic in the sub-image as the image size of the sub-image becomes closer to an upper limit value.

10. The endoscopic image processing apparatus according to claim 8, wherein the acquired information is related to luminance of an entirety of the display image, and
    the processor is configured to:
       increase an indicating level of a second indicating characteristic of the second marker in the sub-image as the brightness of the entirety of the display image becomes closer to a lower limit value; and
       reduce indicating level of the second indicating characteristic in the sub-image as the brightness of the entirety of the display image becomes closer to an upper limit value.

11. The endoscopic image processing apparatus according to claim 1, wherein the determining of the first marker and second marker is determined based on at least one of a state of the one or more candidate regions, a work state, received by the processor, of a user who performs work using an endoscope, or a display state of a display apparatus.

12. The endoscopic image processing apparatus according to claim 2, wherein the metric is determined based on at least one of a type of a lesion included in the one or more candidate regions, a size of the one or more candidate regions in the endoscopic image, a position of the one or more candidate regions in the endoscopic image, a texture and a shape of the one or more candidate regions, a strength of an edge in a boundary portion of the one or more candidate regions, and a color of the one or more candidate regions.

13. The endoscopic image processing apparatus according to claim 1, wherein the first marker surrounds the one or more candidate regions in the main image, and the second marker surrounds the one or more candidate regions in the sub-image.

14. The endoscopic image processing apparatus according to claim 1, wherein the main image comprises a first main image, the sub-image comprises a first sub-image, the one or more candidate regions comprises one or more first candidate regions, and
    the at least one processor is configured to:
       generate a second main image based on a second endoscopic image;
       generate a second sub-image based on the second endoscopic image; and
       using image processing of one or more second candidate regions in the second endoscopic image, determine a third marker of the second sub-image;
    generate a second image including the second main image, the second sub-image, and the third marker overlaid on the second main image to indicate the one or more second candidate regions in the second sub-image with the third marker based on any one of a state of the lesion candidate region, a work state of a user who performs work using the endoscope, or a display state of a display apparatus.

* * * * *